United States Patent
Waksman et al.

(10) Patent No.: US 6,503,185 B1
(45) Date of Patent: Jan. 7, 2003

(54) METHOD AND APPARATUS FOR TREATING A DESIRED AREA IN THE VASCULAR SYSTEM OF A PATIENT

(75) Inventors: Ron Waksman, Atlanta, GA (US); Thomas D. Weldon, Gainesville, GA (US); Richard A. Hillstead, Duluth, GA (US); Jonathan J. Rosen, Alpharetta, GA (US); Charles E. Larsen, Cumming, GA (US); Ian R. Crocker, Stone Mtn., GA (US); Raphael F. Meloul, Atlanta, GA (US)

(73) Assignee: Novoste Corporation, Norcross, GA (US)

( * ) Notice: Subject to any disclaimer, the term of this patent is extended or adjusted under 35 U.S.C. 154(b) by 0 days.

(21) Appl. No.: 09/469,082

(22) Filed: Dec. 21, 1999

Related U.S. Application Data

(62) Division of application No. 08/897,358, filed on Jul. 21, 1997, now abandoned, which is a continuation of application No. 08/330,327, filed on Oct. 27, 1994, now Pat. No. 5,683,345.

(51) Int. Cl.$^7$ .............................. A61N 5/00; G21F 5/02; A61M 31/00
(52) U.S. Cl. ...................... 600/3; 250/497.1; 604/509
(58) Field of Search ................ 128/207.14; 250/497.1; 600/2, 3, 7, 8, 433–435, 470; 604/509, 96.01, 99.03, 915; 623/1.11; 606/192, 194

(56) References Cited

U.S. PATENT DOCUMENTS

| | | | | |
|---|---|---|---|---|
| 1,406,509 A | * | 2/1922 | Viol ............................ 600/7 |
| 1,786,373 A | * | 12/1930 | Walker ......................... 600/2 |
| 2,750,517 A | * | 6/1956 | Baum ...................... 250/497.1 |
| 3,351,049 A | * | 11/1967 | Lawrence ..................... 600/8 |
| 4,655,746 A | * | 4/1987 | Daniels et al. .............. 604/509 |
| 4,669,463 A | * | 6/1987 | McConnell ............ 128/207.14 |
| 4,768,507 A | * | 9/1988 | Fischell et al. ............. 623/1.11 |
| 4,955,895 A | | 9/1990 | Sugiyama et al. .......... 606/194 |
| 5,209,730 A | | 5/1993 | Sullivan |
| 5,213,561 A | | 5/1993 | Weinstein et al. |

(List continued on next page.)

FOREIGN PATENT DOCUMENTS

| | | |
|---|---|---|
| DE | 91 02 312.2 U1 | 8/1992 |
| EP | 0152124 * | 8/1985 |
| EP | 0433011 A1 * | 6/1991 |
| EP | 0448004 A2 * | 9/1991 |
| EP | 829 271 A2 | 3/1998 |

OTHER PUBLICATIONS

European Search Report for European Patent Application No. EP 02 00 8306, dated May 7, 2002.

*Primary Examiner*—Max F. Hindenburg
*Assistant Examiner*—Nikita R Veniaminov
(74) *Attorney, Agent, or Firm*—Cook, Alex, McFarron, Manzo, Cummings & Mehler, Ltd.

(57) ABSTRACT

Apparatus and method are described for delivery of a treating element, such as a radiation source, through a catheter to a desired site in the vascular system of a patient, such as a coronary artery, for inhibiting the formation of scar tissue such as may occur in restenosis following balloon angioplasty. The apparatus includes an elongated flexible catheter tube having proximal and distal end portions, with a lumen extending therebetween, and a diameter sufficiently small for insertion in to a patient's vascular system. One or more treating elements, such as a capsule or pellet containing radioactive material, is positionable within the lumen and movable between the proximal and distal end portions under the force of liquid flowing through the lumen. A method for using such apparatus, including a method for using such apparatus simultaneously with a balloon angioplasty procedure, is disclosed.

27 Claims, 12 Drawing Sheets

U.S. PATENT DOCUMENTS

| | | | |
|---|---|---|---|
| 5,224,933 A | * 7/1993 | Bromander | 604/99.03 |
| 5,302,168 A | * 4/1994 | Hess | 600/3 |
| 5,334,154 A | 8/1994 | Samson et al. | 604/102 |
| 5,413,557 A | 5/1995 | Solar | 604/96 |
| 5,503,613 A | * 4/1996 | Weinberger | 600/3 |
| 5,540,659 A | 7/1996 | Teirstein | 604/104 |
| 5,545,137 A | 8/1996 | Rudie et al. | 604/96 |
| 5,556,389 A | 9/1996 | Liprie | 604/264 |
| 5,618,266 A | 4/1997 | Liprie | 604/21 |
| 5,624,392 A | 4/1997 | Saab | 604/43 |
| 5,643,171 A | 7/1997 | Bradshaw et al. | 600/1 |
| 5,840,064 A | 11/1998 | Liprie | 604/96 |

* cited by examiner

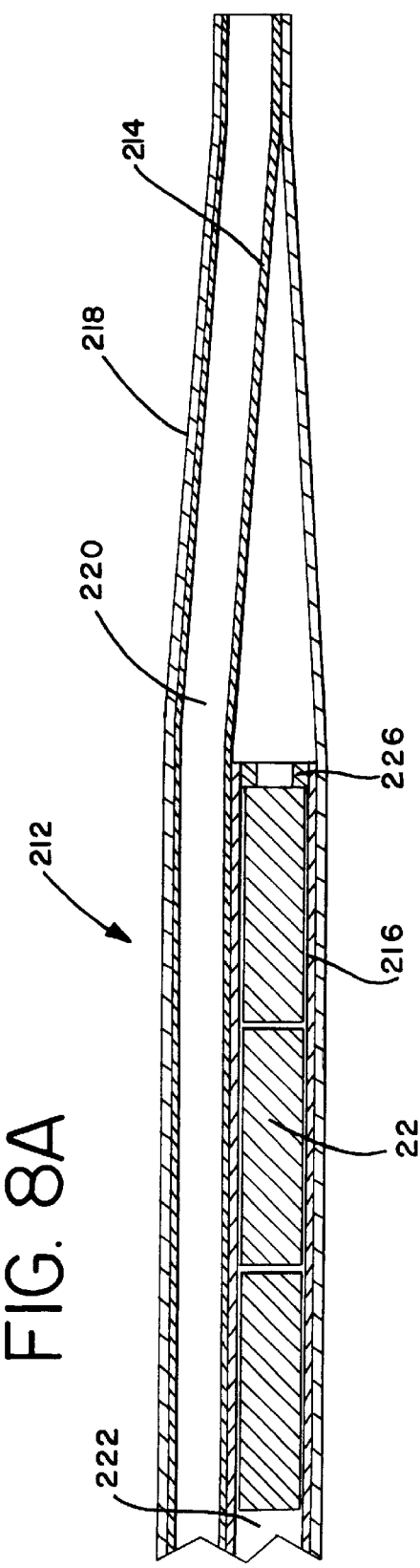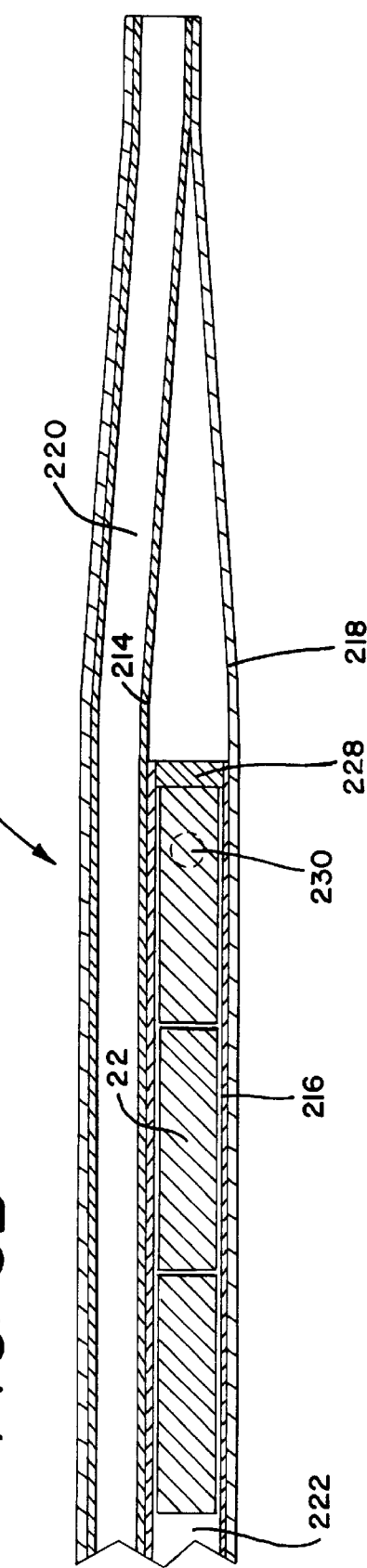

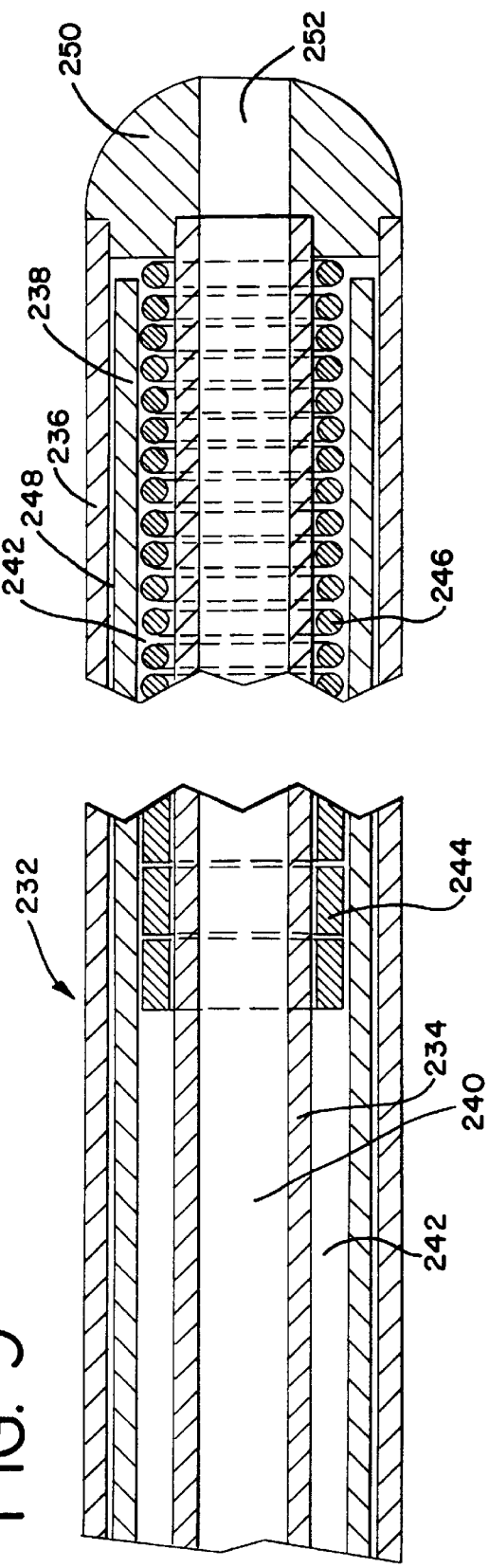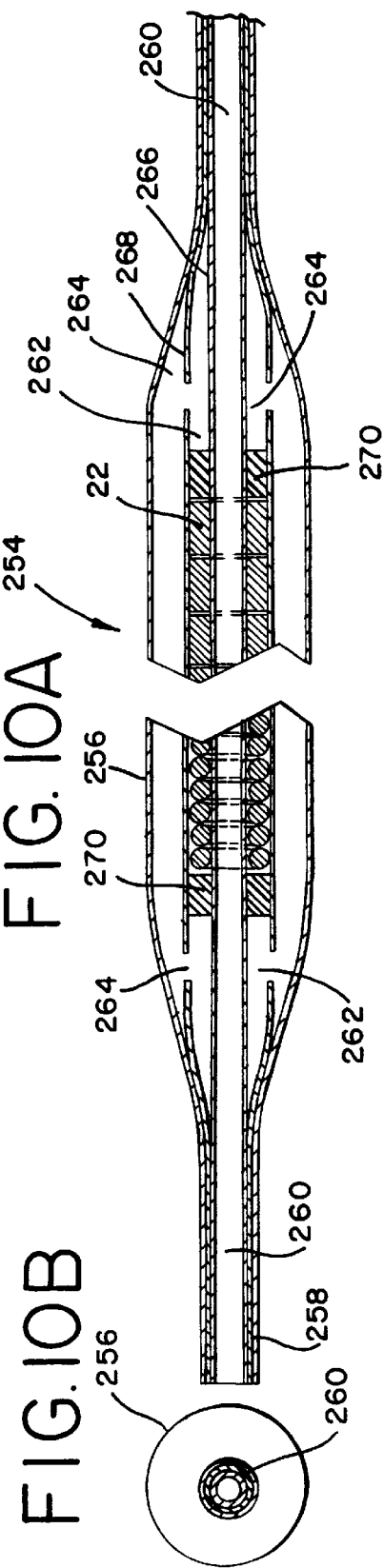

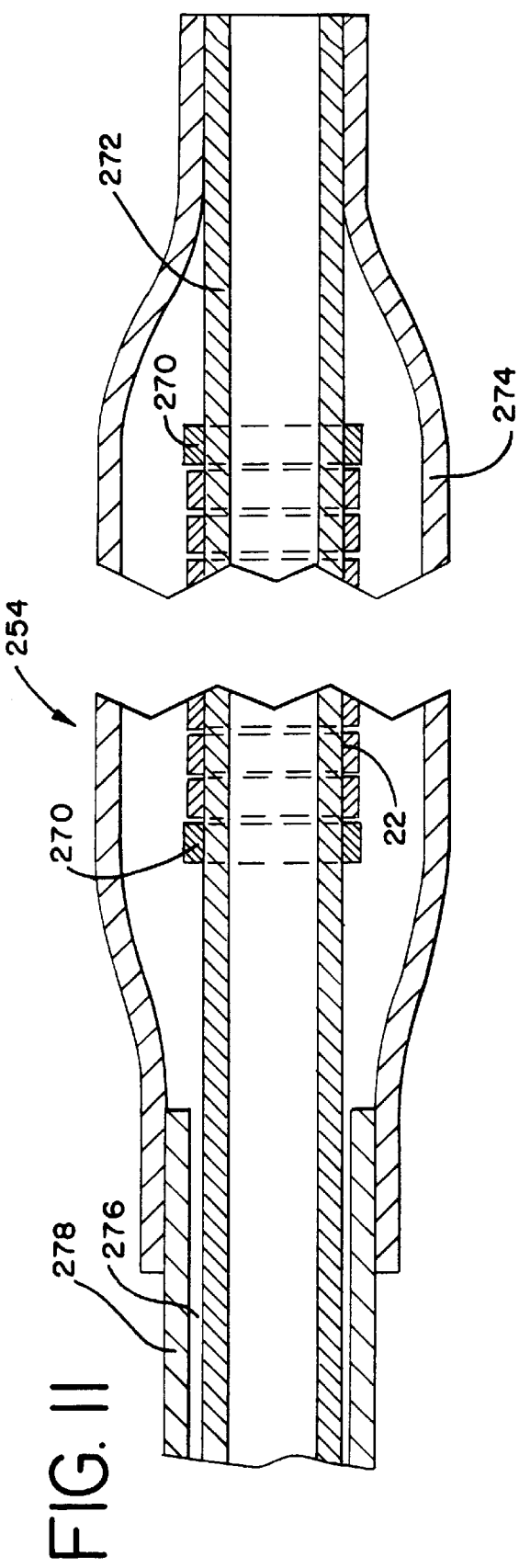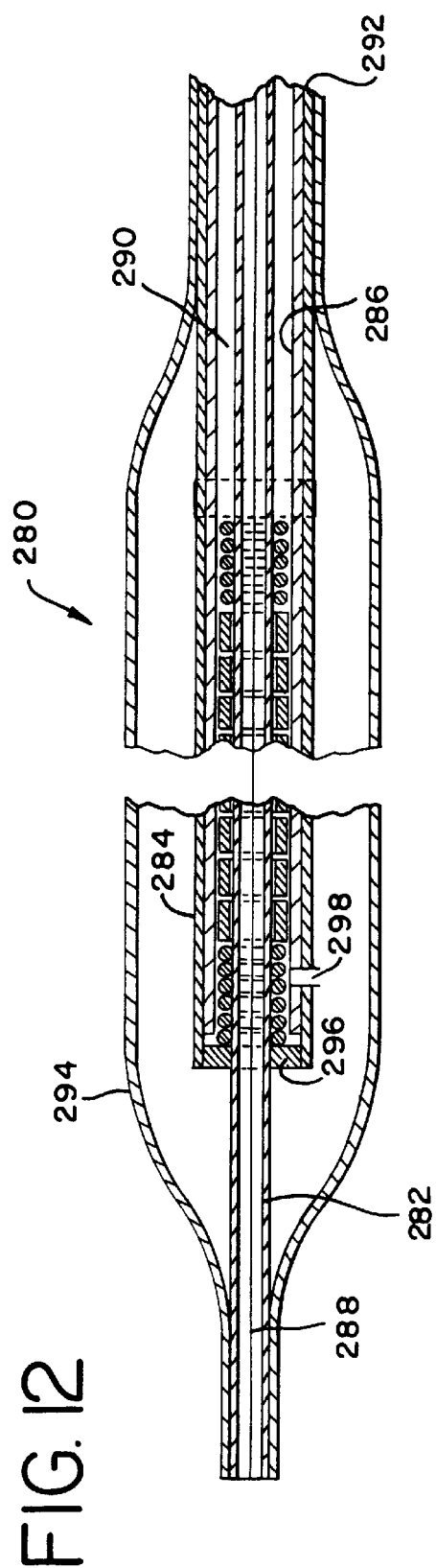

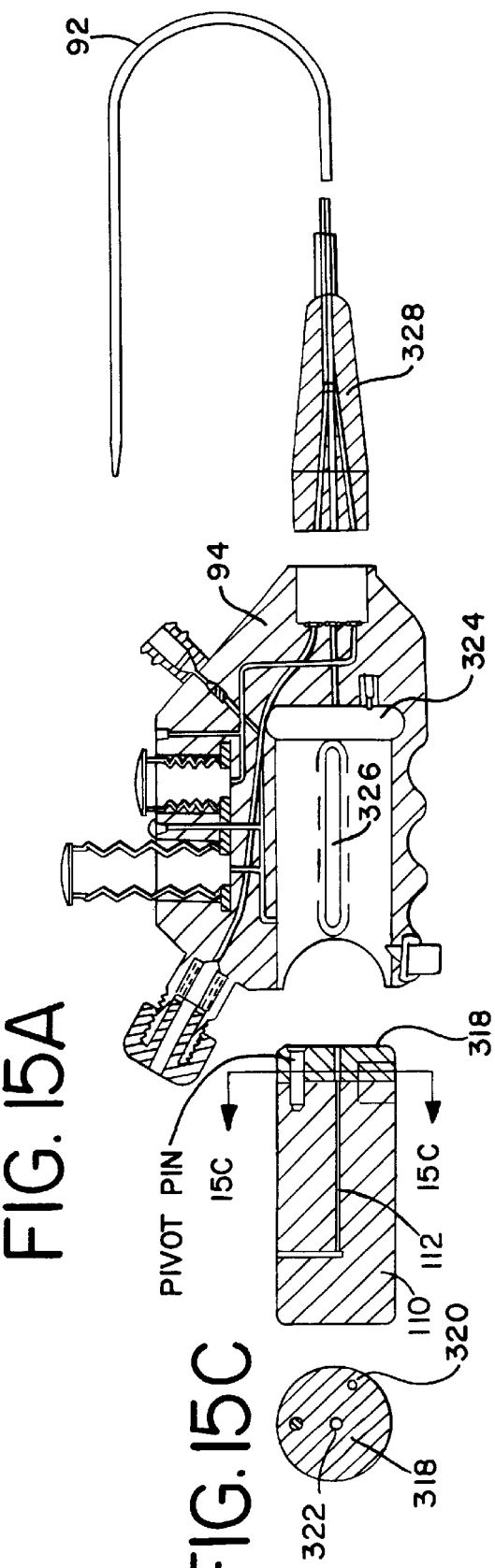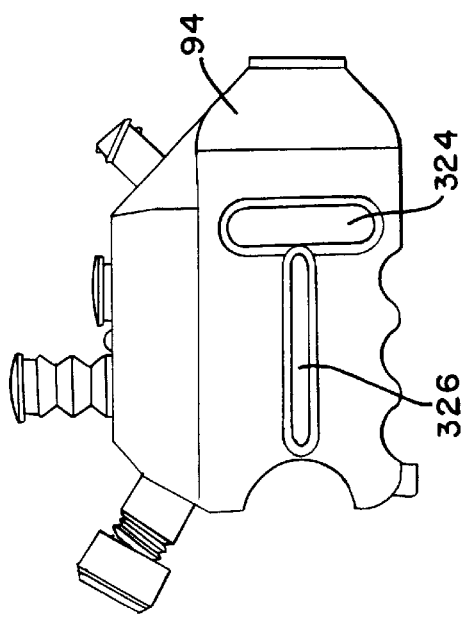

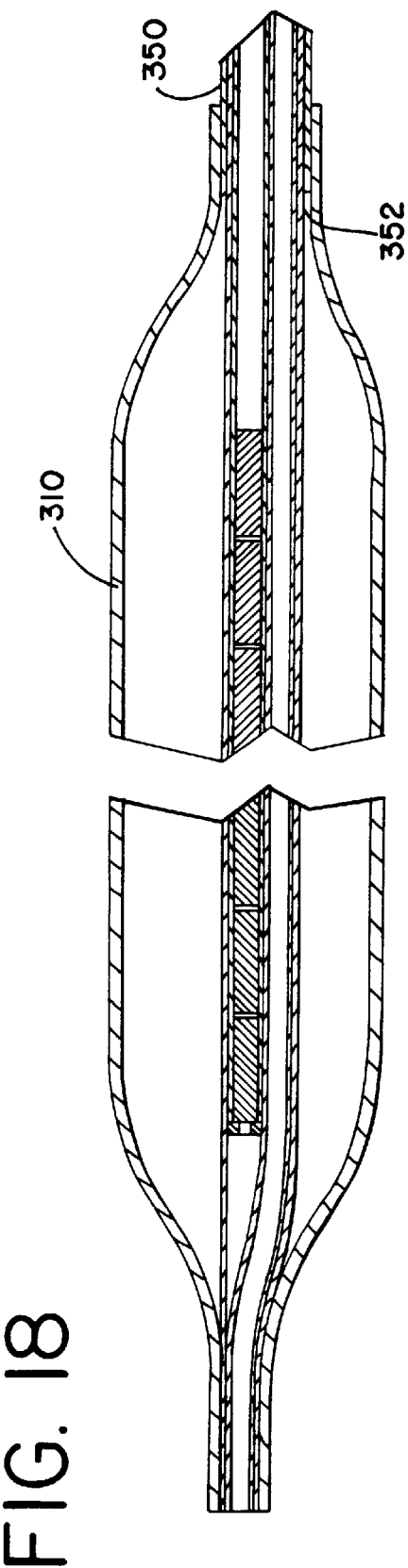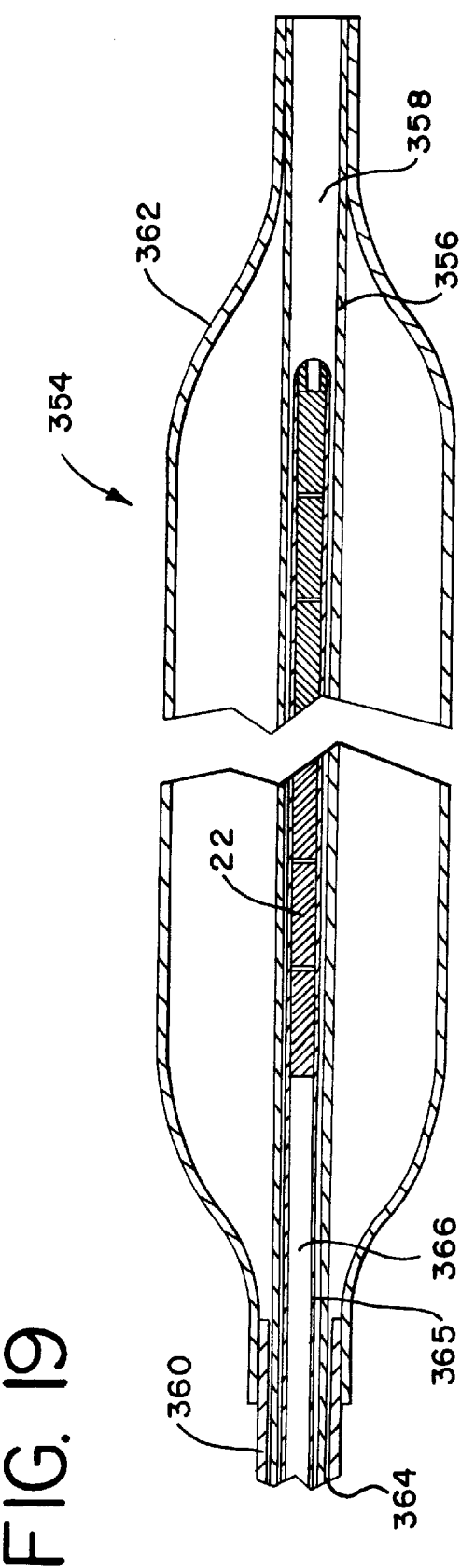
FIG. 18
FIG. 19

METHOD AND APPARATUS FOR TREATING A DESIRED AREA IN THE VASCULAR SYSTEM OF A PATIENT

CROSS REFERENCE TO RELATED APPLICATION

This application is a division of Ser. No. 08/897,358, filed Jul. 21, 1997, abandoned on Aug. 16, 2002 which is a continuation of application Ser. No. 08/330,327, filed Oct. 27, 1994 now U.S. Pat. No. 5,683,345, issued Nov. 4, 1997.

FIELD OF THE INVENTION

The present invention relates generally to the delivery of treating elements by a catheter to a selected site within the vascular system of a patient. More particularly, the present invention relates to method and apparatus for the delivery of a treating element, such as a radiation source, through a catheter to a desired site, such as a coronary artery, for inhibiting wound healing response, such as restenosis following balloon angioplasty.

BACKGROUND OF THE INVENTION

It is known that the human body's healing response to wounds typically includes the formation of what is commonly called scar tissue. This response also occurs within the vascular system of a person following injury to a blood vessel. An injury that provokes the formation of scar tissue may occur in various locations within the vascular system, such as in the carotid artery or in coronary bypasses, or in various ways, such as trauma from surgical or diagnostic procedures.

One area of the vascular system of particular concern with respect to such injuries is coronary arteries that are subjected to procedures for removing or reducing blockages due to plaque within the arteries. Partial and even complete blockage of coronary arteries by the formation of an atherosclerotic plaque is a well known and frequent medical problem. Such blockages may be treated using atherectomy devices, which mechanically remove the plaque; hot or cold lasers, which vaporize the plaque; stents, which hold the artery open; and other devices and procedures which have the objective of allowing increased blood flow through the artery. The most common such procedure is the percutaneous transluminal coronary angioplasty (PTCA) procedures—more commonly referred to as balloon angioplasty. In this procedure, a catheter having an inflatable balloon at its distal end is introduced into the coronary artery, the uninflated balloon is positioned at the stenotic site and the balloon is inflated. Inflation of the balloon disrupts and flattens the plaque against the arterial wall, and stretches the arterial wall, resulting in enlargement of the intraluminal passageway and increased blood flow. After such expansion, the balloon is deflated and the balloon catheter removed.

PTCA is a widely used procedure and has an initial success rate of between 90 and 95 percent. However, long term success of PTCA (as well as the other artery-opening procedures referred to above) is much more limited, due largely to restenosis, or re-closing of the intraluminal passageway through the artery. Restenosis, wherein the vessel passageway narrows to approximately 50% or less of the enlarged size, is experienced in approximately 30 to 50 percent of the patients within six months after PTCA. Restenosis may occur for various reasons, but it is now believed that restenosis is, in significant part, a natural healing response to the vessel injury caused by inflation of the angioplasty balloon.

Vessel injury may occur in several ways during PTCA, including: denudation (stripping) of the endothelium (the layer of flat cells that line the blood vessels); cracking, splitting and/or disruption of the atherosclerotic plaque and intima (innermost lining of the blood vessel); dehiscence (bursting) of the intima and the plaque from the underlying media; stretching and tearing of the media and adventitia (outside covering of the artery) which may result in aneurysmal expansion; and injury to the vessel smooth muscle. Such injury to the vessel typically initiates the body's own natural repair and healing process. During this healing process, fibrin and platelets rapidly accumulate in the endothelium, and vascular smooth muscle cells proliferate and migrate into the intima. The formation of scar tissue by smooth muscle proliferation, also known as intimal hyperplasia, is believed to be a major contributor to restenosis following balloon angioplasty of the coronary artery.

Prior attempts to inhibit restenosis of coronary arteries have included, among other things, the use of various light therapies, chemotherapeutic agents, stents, atherectomy devices, hot and cold lasers, as well as exposure of the stenotic site to radiation. These therapies have had varying degrees of success, and certain disadvantages are associated with each of these therapies. Although radiation therapy has shown promise, particularly in inhibiting intimal hyperplasia, the devices available for delivery of radiation sources to a stenotic site have been limited and have tended to suffer from drawbacks which limit their usefulness. Typical of the devices using radiation to treat restenosis are those shown or described in U.S. Pat. No. 5,059,166 to Fischell; U.S. Pat. No. 5,213,561 to Weinstein; U.S. Pat. No. 5,302,168 to Hess, U.S. Pat. No. 5,199,939 to Dake; U.S. Pat. No. 5,084,002 to Liprie; and U.S. Pat. No. 3,324,847 to Zoumboulis.

SUMMARY OF THE INVENTION

The present invention is directed to apparatus and methods for delivering one or more treating elements, such as a radiation source, through a catheter to a desired location in the vascular system of a human patient and to retrieving the treating element(s) through the catheter, if so desired. The present invention is particularly applicable, but not limited, to the treatment of coronary arteries that have been or will be subjected to PTCA or other artery-opening procedures, in order to inhibit intimal hyperplasia and reduce the risk of restenosis. The present invention is also useful in other areas of the vascular system, such as in the carotid artery or in coronary bypasses.

More specifically, as set forth in the appended claims, the present invention comprises an elongated flexible catheter tube having a proximal end portion adapted to remain outside the patient's body, a distal end portion adapted to be positioned at a selected location within the vascular system of the patient and a lumen extending therebetween, with the diameter of the catheter tube being sufficiently small for insertion into the patient's vascular system. The catheter tube is preferably but not necessarily adapted for positioning the distal end of the tube at the desired site by advancement over a guide wire. A port is provided at the proximal end portion of the tube, through which blood-compatible liquid may be introduced from a source of such liquid into the lumen. One or more treating elements, which may be in the form of a solid capsule, pellet or the like, such as a capsule or pellet containing radioactive material, is positionable within the lumen and is movable between the proximal and the distal end portions of the tube under the motive force exerted by the liquid flowing through the lumen.

In accordance with the present invention, a method is also provided for treating a selected area in the vascular system of a patient wherein an elongated flexible catheter tube having a distal end portion adapted to be positioned at a selected location within the vascular system of the patient, a proximal end portion adapted to remain outside the patient's body, a lumen extending therebetween, and a diameter sufficiently small for insertion into the patient's vascular system is introduced into the vascular system of a patient. The catheter is preferably but not necessarily introduced over a guide wire until the distal end portion of the tube is within the selected area of the vascular system. A port communicating with the first lumen is adapted for introduction of blood-compatible liquid into the lumen. One or more treating elements, such as a capsule or pellet containing radioactive material, is introduced into the lumen at the proximal end portion of the tube and is moved from the tube's proximal end portion through the lumen to the distal end portion within the selected area by flowing the blood-compatible liquid through the lumen to generate a motive force on the element so as to move it from the proximal end to the desired location at the distal end portion. There, the treating element is allowed to remain a sufficient time for treatment of the selected area, during which time the remaining portion of the catheter is free of treating elements so as to not unnecessarily expose other tissue to such treatment. After the treatment is completed, the catheter tube is removed from the patient.

In another embodiment, the present invention is embodied in an angioplasty balloon catheter having proximal and distal end portions, with a lumen extending therebetween. The lumen communicates with an inflatable balloon located on the distal end portion. In accordance with the present invention, one or more treating elements, such as a radiation source, is either carried fixedly at the balloon or moved through a lumen from the proximal end portion to the distal end portion, for delivery of radiation to the stenotic site as the angioplasty procedure is actually carried out—therefore allowing what may otherwise be a two-step process to be carried out in a single step. From this summary, it should be apparent that the method of the present invention may be carried out before, during or after an angioplasty or other artery-opening procedure, whichever is deemed most desirable by the treating physician.

DRAWINGS

FIG. 8A is a partial cross-sectional view of a fifth embodiment of the elongated catheter tube of the present invention, showing the treating elements in the distal end portion of the tube.

FIG. 8B is a partial cross-sectional view of a modified version of the embodiment of the elongated catheter tube of FIG. 8A, showing the treating elements in the distal end portion of the tube.

FIG. 9 is a partial cross-sectional view of a sixth embodiment of the elongated catheter tube of the present invention showing toroidal or ring-shaped treating elements in the distal end portion of the tube.

FIG. 10 is a partial cross-sectional view of an alternative embodiment of the present invention having an inflatable balloon and treating elements fixedly positioned on the distal end portion.

FIG. 11 is a partial cross-sectional view of an alternative embodiment of the present invention having an inflatable balloon, with the treating elements disposed therein.

FIG. 12 is a partial cross-sectional view of another alternative embodiment of the present invention having an inflatable balloon, with the treating elements movable along the catheter.

FIG. 15A is a partial cross-sectional view of a further embodiment of the treatment delivery system of the present invention.

FIG. 15B is a elevational view of part of the proximal end portion of the treating system shown in FIG. 15A.

FIG. 15C is a cross-sectional view taken along lines 15c—15c of FIG. 15A.

FIG. 18 is a partial cross-sectional view of still another alternative embodiment of the present invention having an inflatable balloon, with the treating elements movable along the catheter.

FIG. 19 is a partial cross-sectional view of still another alternative embodiment of the present invention having an inflatable balloon, with the treating elements movable along the catheter.

DETAILED DESCRIPTION

Figure 1:
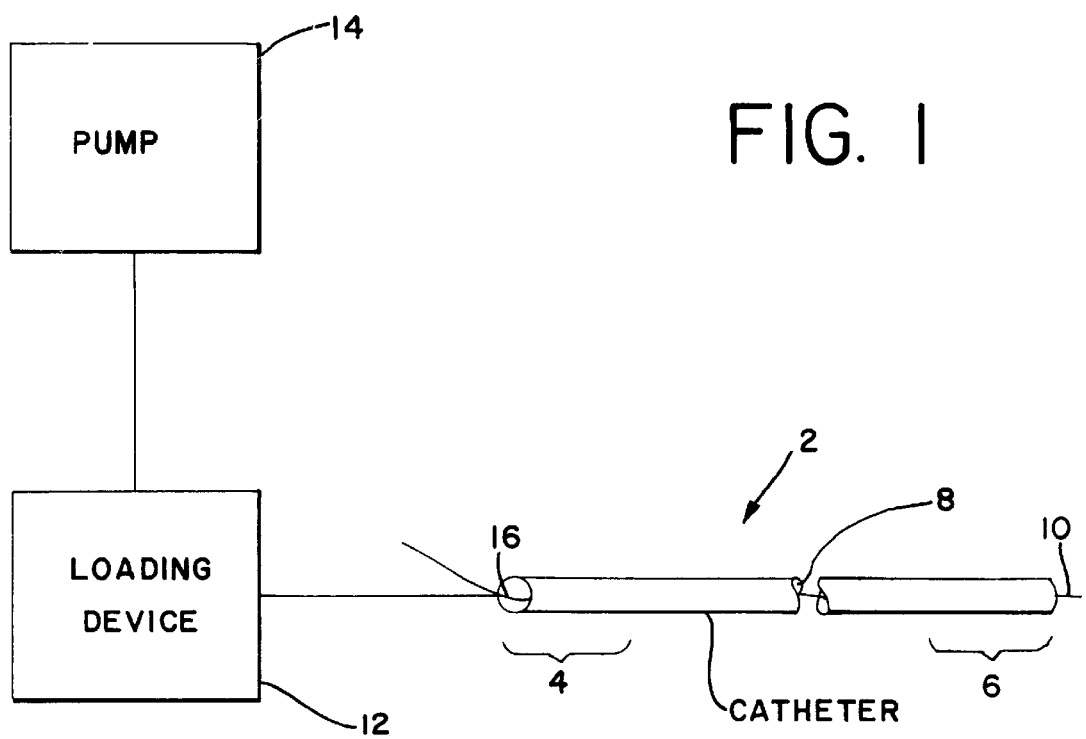
FIG. 1 is a diagrammatic representation of a catheter-based treatment delivery system embodying the present invention.

FIG. 1 depicts one embodiment of the present invention in general diagrammatic form for ease of initial understanding. Shown in FIG. 1 is an elongated catheter 2 having a proximal end portion 4, a distal end portion 6, and at least one lumen 8 extending therebetween. The catheter is sized for insertion of the distal end portion through the vascular system of a patient to a selected area to be treated, such as the site of a balloon angioplasty procedure or other opening procedure, such as an atherectomy, in a coronary artery. This may be carried out, for example, by inserting the catheter percutaneously into a femoral artery and advancing the catheter over a typical guide wire 10 upwardly through the descending aorta, over the aortic arch, downwardly through the ascending aorta and into the particular coronary artery that has been selected for treatment, such as a coronary artery that has been subjected to PTCA or other artery-opening procedure. Guide wires and procedures used in advancing such a catheter to the point of the angioplasty procedure are well known and will not be discussed in detail.

At the proximal end of the catheter, which is located outside the patient in a percutaneous procedure such as described above, a transporting and/or loading device 12 is provided for loading a treating element, such as a pellet or capsule comprising or containing radioactive material, into the lumen 8 of the catheter 2. Additional treating elements may also be loaded such that the total length of the combined treating elements corresponds to at least the length of the stenotic area of the vasculature to be treated. The total length of the combined treating elements also could be longer than the stenotic area in order to assure that the end edges of the stenotic area are also treated. This loading procedure may also be performed manually, but a mechanical loader as described in more detail later is preferred to provide better user protection against radiation.

After the treating element is loaded into the lumen 8, pressurized blood-compatible liquid, such as sterile saline solution or sterile water, is introduced via liquid source 14 through a port 16 in the proximal end of the lumen behind the treating element. Flow of liquid through the lumen pushes the treating element along the lumen to the distal end portion, which is located at the site to be treated. The liquid which provides the motive force for moving the treating element may be allowed to exit from the distal end of the catheter or may be returned in a parallel lumen provided in the catheter or may be returned via suction through the same lumen in which the treating element travels.

After the treating element is located at the desired site, the treating element is allowed to remain for a time sufficient to treat the tissue. For radiation treatment of a stenotic site, the treating element preferably are beta-emitting radiation sources, and the residence time period will be relatively short, on the order of minutes as discussed in more detail below.

After the treatment is complete, the catheter may be removed with the treating element remaining at the distal end or, alternatively, liquid may be forced through the lumen in a reverse direction to return the treating element to the proximal end and into the loading device, if desired, before removal of the catheter. The reverse flow of fluid may be achieved by forcing liquid under positive pressure through the lumen in a reverse direction or by applying a suction, such as by withdrawing the piston of a syringe attached at the proximal end of the lumen, to the lumen.

The transporting/loading device 12 need not be connected directly to the proximal end of the catheter 2 if such direct connection would result in possible kinking of the catheter or would restrict maneuverability. In that case, an additional length of tubing (which may have the same number of lumens as the catheter) could be provided between the transporting/loading device 12 and the proximal end portion of the catheter. In such event, the additional length of tubing (as well as the proximal end portion of the catheter located outside the patient) may be shielded to protect the user and/or the patient from unnecessary radiation exposure.

Figure 2A:
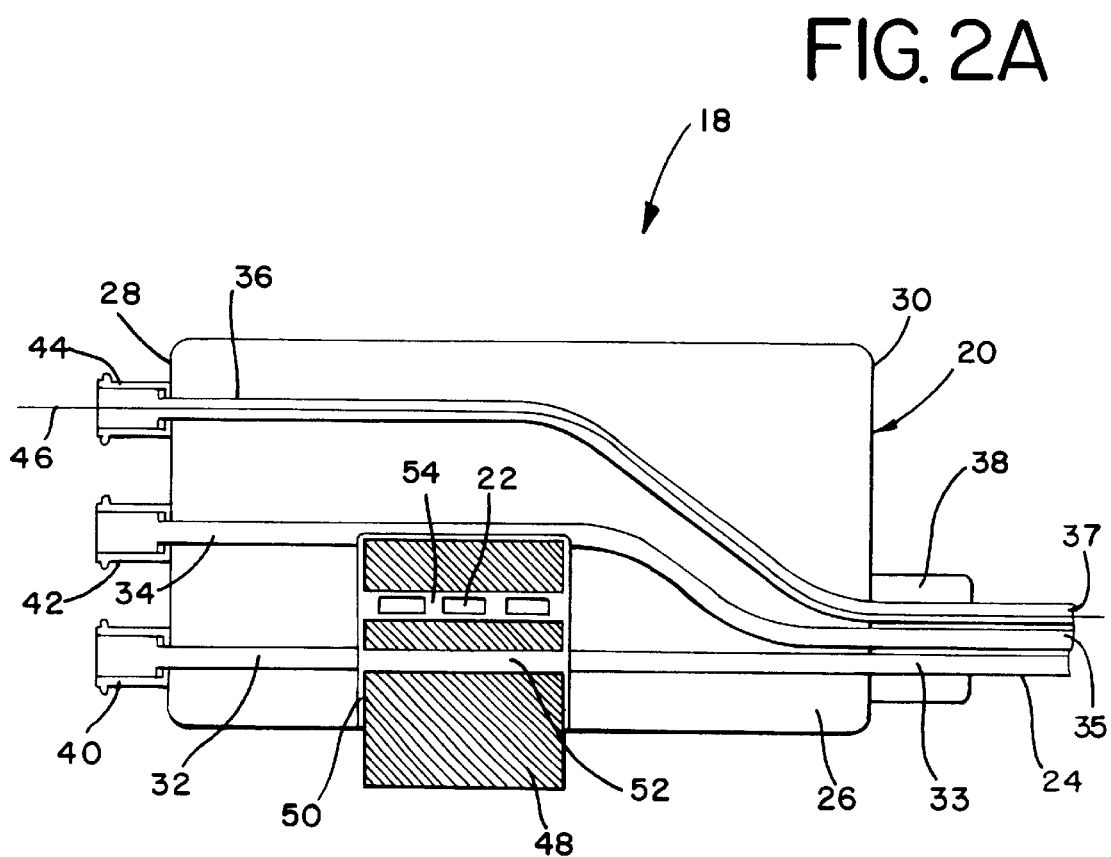
FIG. 2A is cross-sectional view of one embodiment of the proximal end portion of the treatment delivery system of the present invention.

FIG. 2A shows one actual embodiment of the proximal end of the catheter system depicted in FIG. 1. Although not limited to use with radioactive treating elements, the device shown in FIG. 2A is particularly adapted for that application.

Specifically, FIG. 2A depicts a three-lumen catheter system 18 with a loading device 20 containing treating elements 22 and connected to the proximal end of a three lumen catheter tube 24. The loading device comprises a rigid body 26 preferably of a suitable rigid polymer, having a proximal end 28, a distal end 30 and a first, a second and a third bore, 32, 34 and 36 respectively, extending therebetween. A fitting 38 located at the distal end of the body connects the first, second and third bores, respectively, with one of the three lumens 33, 35 and 37 of the catheter tube 24.

At the proximal end of the housing member, ports, such as luer connector ports, are provided for communication with bores 32, 34 and 36. A first port 40 is aligned with the first bore 32 of the body and is adapted for the entry or exit of a liquid, such as sterile saline. A second port 42 is in communication with the second bore 34 of the housing member and is likewise adapted to permit the entry or exit of liquid into the body. The third port 44 opens into the third bore of the body and is adapted to receive a guide wire 46 to aid in positioning the distal end of the catheter tube within a patient. A valve (not shown), such as a Touhy-Borst valve, may be attached to the third port to prevent leakage of fluid around the guide wire during or after insertion of the device into the patient.

For loading and/or unloading of the treating elements 22, a retaining device such as a magazine, carrier or carriage 48 is slidably positioned within a slot 50 defined in the body 26 intermediate the proximal and distal ends. The carriage is preferably constructed of the same material as the rigid body 26 and has a first through bore 52 and a second through bore 54. The first and second through bores of the carriage may be selectively aligned with the first bore 32 of the body, depending upon the lateral position of the carriage relative to the body. A carriage with only a single through bore may also be used.

By pre-loading the treating elements into the carriage, they may be conveniently handled, shipped and stored separate from the rest of the loading device. When the user is ready for the procedure, the carriage may be simply inserted into the body, thereby minimizing handling of the treating elements by and exposure to the user. The carriage is preferably made of a material and has sufficient thickness to protect the user against unnecessary exposure to radiation when the treating elements are radioactive.

As shown in FIG. 2A, carriage 48 is fully inserted into the body 26, with the first bore 52 of the carriage aligned with the first bore 32 of the body. In this position, second bore 54 of the carriage contains the treating elements 22 and is positioned within the body, thereby providing protection of the user from radiation emitted by the treating elements. In this first position, fluid, such as sterile saline, may be introduced through the first port to prime the body and catheter and remove any air contained therein, if so desired.

By sliding the carriage 48 outwardly from the body 26, the carriage is moved into a second position wherein second bore 54 of the carriage is coaxially aligned with first bore 32 of the body, and the treating elements 22 are ready for introduction into the catheter 24. In this second position, pressurized liquid, such as sterile saline, may be introduced via pump 14 through first port 40 to supply the motive force against the treating elements 22, ejecting them from second through bore of the carriage, distally through the first bore 32 of the body, and into a lumen of the catheter.

The specific design of the pump 14 may be chosen from various alternatives. For example, the pump 14 may be a simple saline-filled piston syringe attached via luer lock connector to port 40 of body 26. Manual depression of the syringe plunger would provide sufficient force to eject the treating elements and move them to the desired position in the catheter (and withdrawal of the plunger may assist in returning the treating elements to the proximal end portion after the treatment is complete). Alternatively, the motive force may be provided by a column of liquid from a suspended container of sterile saline or water, controlled by a simple roller clamp or stopcock.

Alternative configurations for the carriage (not shown) also may be used without departing from the scope of the present invention. For example, the carriage may be cylindrical and/or rotatably mountable within the body. Through bores or chambers within the carriage may be selectively brought into alignment with the bores of the body by rotating the carriage. The treating elements may be pre-loaded in the cylinder to minimize user contact and to protect the user from radiation when a radioactive treating element is employed. By providing the treating elements 22 pre-loaded into a loading device 20 or pre-loaded into a carriage 48 that may be inserted into a loading device, user contact with the treating elements is minimized, and for radioactive treating elements, the user may be shielded from radiation.

Figure 2B:
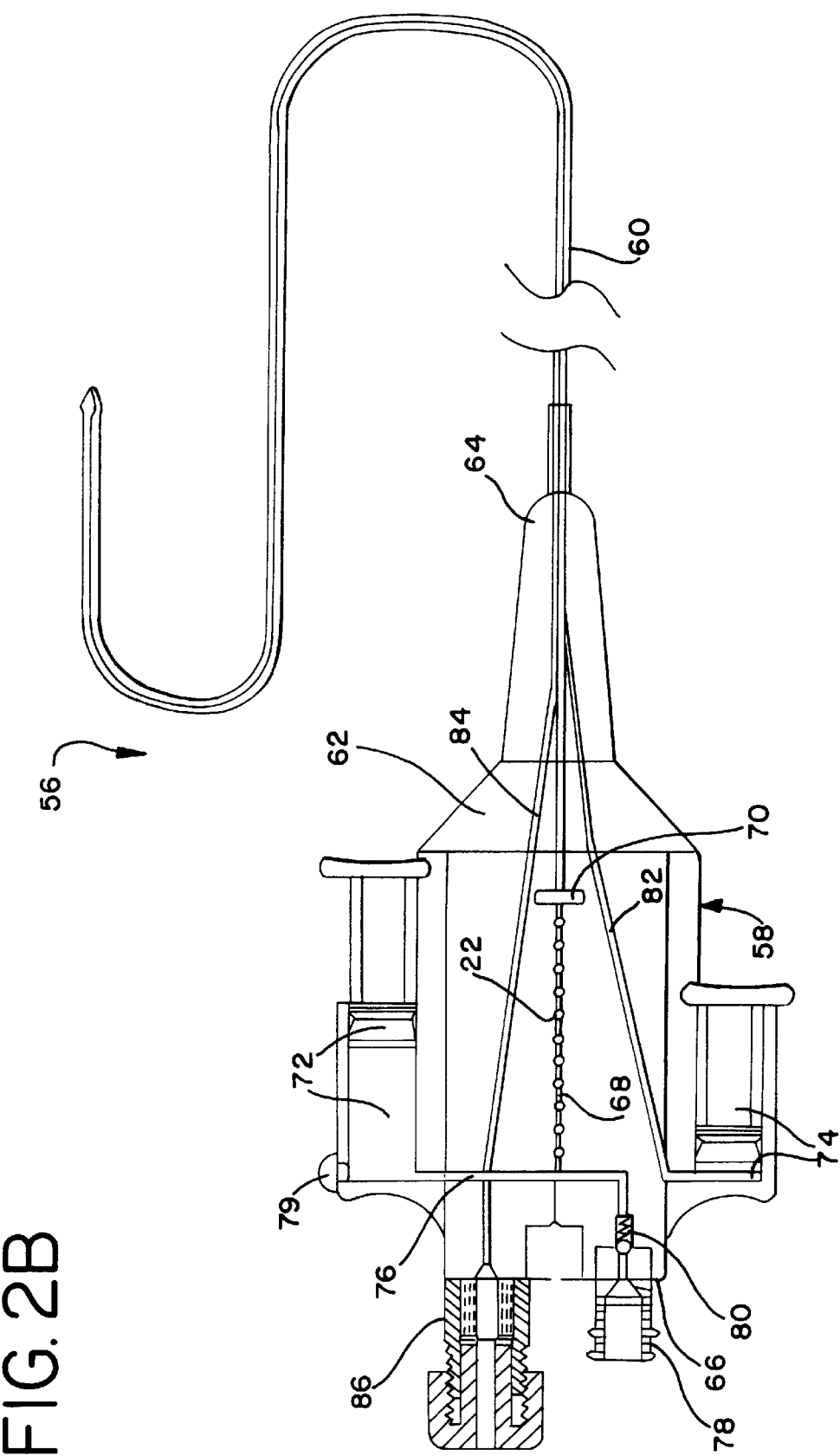
FIG. 2B is a cross-sectional view of another embodiment of the treatment delivery system of the present invention.

FIG. 2B shows a further alternative embodiment of a catheter system of the present invention. Catheter system 56 includes a combination loading device and pump 58 and a multi-lumen catheter 60. The combination pump and loading device comprises a body portion 62 having a distal end portion 64 attached to the elongated catheter tube and a proximal end portion 66 mounting connectors for fluid communication with passageways defined in the body.

The body portion 62 has a central bore or passageway 68 in which treating elements 22 are located prior to the treatment and after the treatment is completed. The central bore 68 communicates directly with one of the lumens of multi-lumen catheter 60. Discharge of the treating elements from the bore 68 is controlled by gate 70, which may be moved between positions blocking flow or allowing flow through central bore. Alternatively, the gate may contain openings of sufficiently small size to permit fluid to pass therethrough, while preventing passage of the treating elements while the gate blocks the central bore. This aids in priming the system with the treating elements in position in bore 68, if so desired.

For providing the pressurized flow of liquid to transport treating elements to and from the distal end of catheter 60, a pair of piston-cylinder arrangements are provided on opposite sides of the body portion 62. Piston-cylinder arrangement 72 provides the liquid flow for dispatching the treating elements to the distal end of the catheter and piston-cylinder arrangement 74 provides the reverse liquid flow for retrieving the treating elements therefrom.

Interior passageway 76 in the body 62 communicates between liquid inlet port 78, central bore 68 and the cylinder of dispatch piston-cylinder arrangement 72, which provides the fluid flow for moving the treating elements into and along a principal lumen of the catheter 60. One-way, spring loaded ball valve 80 within passageway permits liquid to enter through the inlet port but blocks liquid from exiting from the port. Vent 79 allows displacement air to exit from the passageway 76 when liquid is added, for priming purposes and the like, and a pressure relief valve 81 may be provided to prevent overpressurization of the catheter.

Interior passageway 82 in the body 62 communicates between the cylinder of the retrieval piston-cylinder arrangement 74 and a return lumen of the catheter 60. At the distal end portion of the catheter, the return lumen communicates with the principal lumen to provide a closed circulation path for the liquid that dispatches and retrieves the treating elements.

In addition, the body 62 has a third interior passageway 84 that communicates between guide wire inlet 86 and a guide wire lumen of the catheter 60. By itself, the catheter 30 may not have sufficient strength or torsional rigidity for insertion along a lengthy serpentine vascular path—in typical angioplasty procedures, the distance between the percutaneous entry point and the coronary artery may be approximately 3–4 feet (90–120 cm). To assist in positioning the distal end of the catheter at the desired location, the catheter may be advanced over a guide wire that is pre-inserted to the desired location in a manner well known to those skilled in performing angioplasty and similar procedures. The guide wire inlet preferably includes a Touhy-Borst valve or similar known device to close the guide wire inlet around the guide wire to restrict leakage of blood or other fluid from the guide wire lumen.

In use, the interior passageways, piston-cylinder arrangements, and catheter principal and return lumen are filled with sterile water or saline through the liquid inlet port 78 and one-way valve 80. In the initial position, the dispatch and retrieval piston-cylinders are oppositely positioned, with the piston of the dispatch piston-cylinder 72 in a withdrawn position, as shown in FIG. 2B, and the piston of the retrieval piston-cylinder 74 in an advanced position, also as shown in FIG. 2B. Before the treating elements can be moved to the desired position, gate 70 controlling the central bore must be opened.

By advancing the dispatch piston, the liquid in the dispatch cylinder is forced through the interior flow path 76 and into the central bore 68 containing the treating elements 22. The pressurized liquid flow ejects the treating elements from the central bore and forces the treating elements along the principal lumen of the catheter to the distal end portion located at the site to be treated. As liquid moves along the principal lumen in a distal direction, it displaces an equal amount of liquid that returns along the return lumen and enters the cylinder of the retrieval piston-cylinder arrangement 74, pushing the retrieval piston outwardly.

Retrieval of the treating elements may be accomplished by reversing the steps described above. The retrieval piston is advanced, forcing liquid in a reverse or distal direction along the return lumen and returning the fluid to the body along the principal lumen. The liquid flow moves the treating elements in a proximal or return direction along the principal lumen, returning them to the central bore of the body 62. The returning liquid enters the cylinder of the dispatch piston-cylinder arrangement 72.

With the catheter system as shown in FIG. 2B, a completely closed system is provided, and no liquid that contacts the treating elements is allowed to enter the patient's body.

This may be particularly important when the treating agent is radioactive. The closed system arrangement also allows the treating elements, whether a single element or a train of treating elements, to be shifted back and forth slightly while in the distal portion of the catheter by alternately slightly depressing the dispatch and retrieval pistons. This technique may be used to provide a more uniform exposure of the selected vessel area, particularly where there is dead space between or at the ends of the treating elements.

Figure 2C:
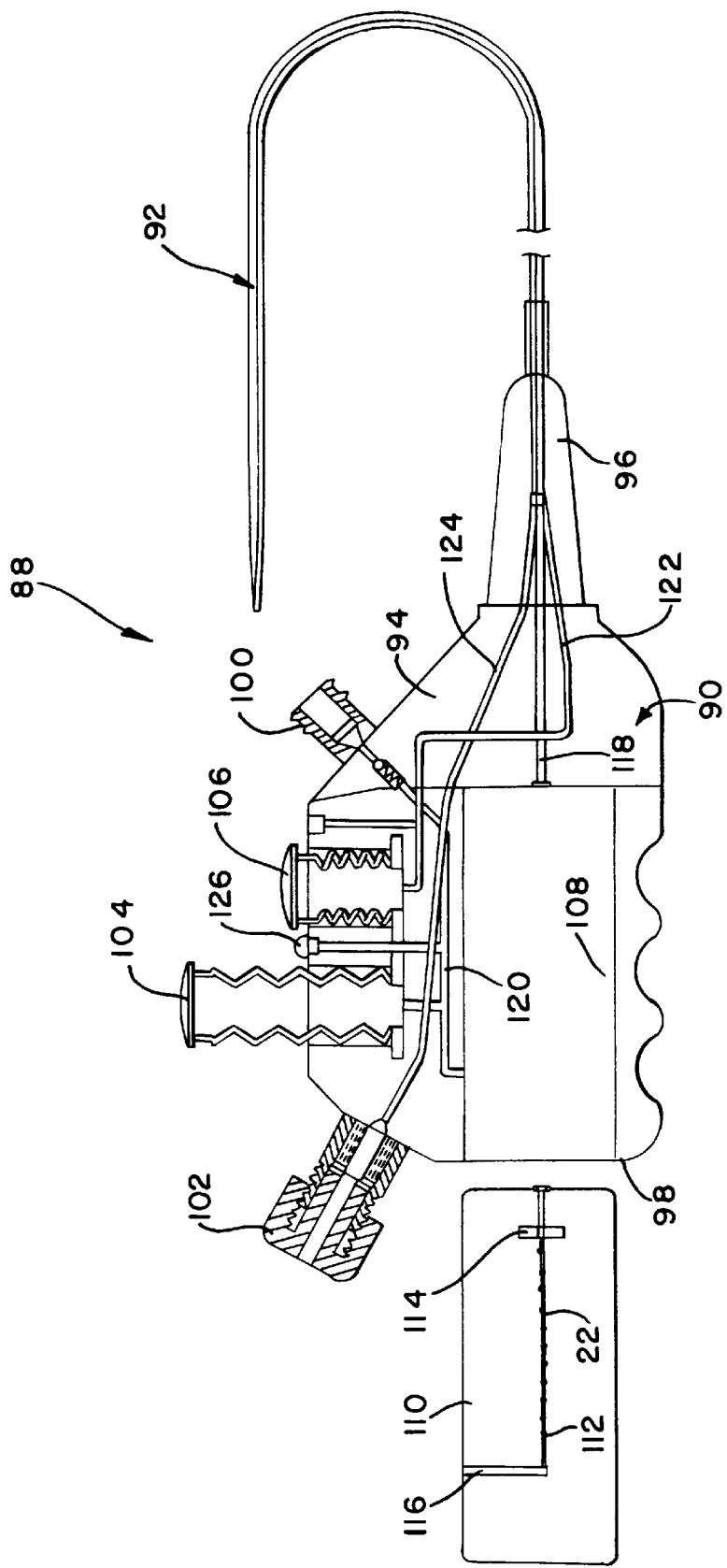
FIG. 2C is a cross-sectional view of still another embodiment of the treatment delivery system of the present invention.

A variation on the catheter system of FIG. 2B is depicted in FIG. 2C. The catheter system 88 shown there similarly includes a combination pump and loading device 90 and a multi-lumen catheter 92. The combination pump and loading device 90 also has a body portion 94 with a distal end portion 96 attached to the catheter 92, and a proximal end portion 98. In this embodiment, however, liquid inlet port 100, guide wire inlet 102 and dispatch and retrieval bellows 104 and 106, respectively, are located on one side of the body 94. This arrangement permits a large cylindrical chamber 108 to be provided, extending inwardly from the proximal end of the body, for receiving a carrier or insert 110 which is pre-loaded with treating elements 22. Alternatively, the body 94 and insert 110 could be of one piece or integral construction.

Insert 110 has a central bore 112 in which the treating elements are located, a gate 114 controlling passage of the treating elements from the central bore, and a laterally extending branch 116 of the central bore. When inserted into the chamber 108 of the body 94, central bore 112 of the insert 110 is aligned with central passageway 118 of the body 94, which communicates directly with a principal lumen of the catheter 92, and branch 116 communicates with internal passageway 120 of the body, which connects to the liquid inlet port 100 and the dispatch bellows 104.

Alternatively, the insert 110 could have a plurality of bores and be rotatably mounted in the body for selective alignment of the bores with inlet port 100 and central passageway 118. In this arrangement, one bore could be empty for fast priming of the system and another bore could contain the treating elements.

As with the embodiment in FIG. 2B, an internal liquid flow passageway 122 is provided in the body 94, communicating between the retrieval bellows and a return lumen of the catheter 92, and a guide wire passageway 124 is provided between a guide wire lumen of the catheter and guide wire inlet 102. Also similarly, a vent 126 is provided in communication with the passageway that connects with the liquid inlet port 100.

In operation, the catheter system of FIG. 2C is essentially identical to that discussed regarding FIG. 2B. The embodiment of FIG. 2C allows the treating elements to be conveniently stored separately from the remainder of the catheter system, for example in special radiation-proof containers.

It should be clear that in each of the embodiments discussed above, the body, carrier (insert or carriage) and catheter may be provided in various combinations of assemblage, as a matter of choice. For example, the body and carrier could be preassembled or even of one piece construction. Similarly, the body could be preassembled with the catheter tube, with the carrier separate for convenient storage and transportation of the treating elements. Alternatively all three elements could be separate and assembled in the desired configuration on site—this would permit the physician to select the appropriate combination depending on the desired procedure.

For radiation exposure of the desired site, the treating elements 22 contain radioactive material, preferably beta-emitting. In the preferred embodiment shown in FIG. 3, the treating elements are elongated hollow cylinders 128 which are preferably constructed of stainless steel, silver, titanium or other suitable material, and are ideally in the range of 2.5 to 5.5 mm in length. The cylindrical treating elements have rounded first and second ends with a chamber 130 extending therebetween. The inner diameter of chamber 130 is preferably in the range of 0.4 to 0.6 mm. A first end plug 132 closes the first end of the cylinder, while a second end plug 134 closes the second end. The end plugs are preferably less than about 1 mm in width and are affixed to cylinder 128, for example, by welding.

The outer diameter of the treating elements is preferably between approximately 0.6 and 0.8 mm, being sized, of course, to slidably fit into the respective receiving bores of the carriages, bodies and catheter lumen described above. To permit maximum mobility through the loading devices and catheters described above, the inner diameter of each of the bores or lumens the treating elements pass through should preferably be less than twice the outer diameter of the cylindrical treating elements and the outer surface of the treating elements may be coated with Teflon material or similar low-friction material to reduce friction between the treating element and the wall of the lumen in which it moves. This allows the treating elements to move quickly through the lumen, minimizes unnecessary exposure of other tissue to the treating elements and in particular minimizes radiation exposure to other tissue. Additionally, to increase the surface area of the treating elements subject to the motive force provided by fluid being passed through the system, the treating elements may also be provided with one or more annular ridges which extend outwardly about the circumference of the treating elements.

Figure 3:
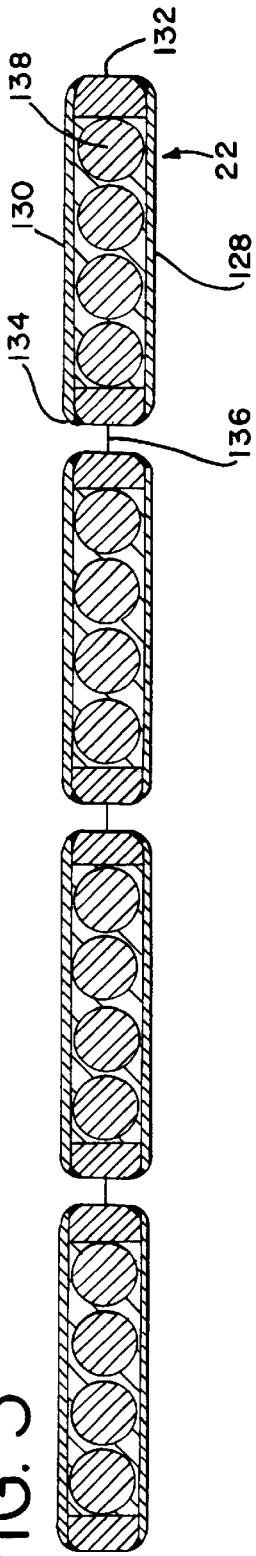
FIG. 3 is a cross-sectional view of one embodiment of the treating elements of the present invention.

To treat a length of vascular tissue, a plurality of treating elements, joined together to form a train of treating elements, as illustrated in the attached figures, may be used. To keep the treating elements uniformly spaced from each other, and, more importantly, to prevent the treating elements from becoming too spaced apart while moving through the catheter, the individual treating elements may be connected by several lengths of hard tempered spring wire 136, as is shown in FIG. 3.

Each treating element 22, as constructed above, encapsulates a therapeutic agent, such as a radiation emitting substance 138. Radiation emitting substance 138 is contained within interior chamber 130 of the treating element and may be composed of any alpha, beta or gamma particle emitting substance. Preferably, however, the radioactive source is a pure beta-particle emitter, or beta and gamma emitter. Examples of such substances include $Strontium^{90}$, $Ruthenium^{106}$, $Phosphorus^{32}$, $Iridium^{192}$, and/or $Iodine^{125}$.

The amount and strength of the radioactive material contained in the combined number of treating elements 22 should be sufficient to deliver a desired dosage of from 100 to about 10,000 rads, preferably about 700 to 5,000 rads, in about 2–10 minutes. Radioactivity is generally measured in units of "Curie" (Ci), and the radioactivity of the material for the present invention is selected to provide the above dosage. For the preferred dosage, the radioactive material may have a radioactivity of approximately 0.45 and 25,000 mCi per centimeter of vessel to be treated, depending on the radiation source used. As described briefly earlier, when a train of treating elements is used which have dead space (non-radioactive) between adjacent elements, the train may be oscillated by moving the catheter slightly back and forth or by briefly repeatedly reversing the flow of liquid, resulting in a shifting back and forth of the treating elements to provide a more uniform radiation exposure of the selected area of the vessel.

The selected radioactive material may be contained within glass, foil, or ceramics, or, alternatively, within a powder or liquid medium, such as microparticles in liquid suspension. When solid materials are used, the preferred outer diameter of the material is approximately 0.5 mm, allowing it to be inserted into the central chamber 130 of the treating element cylinder 128. Such radioactive materials may be formed into pellets, spheres, and/or rods in order to be placed into the chamber of the treating element.

Various alternative treating elements may also be used to contain the radioactive material without departing from the present invention. For example, the treating elements may be toroidal, spherical, or in the form of elongated rings, and in such configurations, the radioactive material may be actually impregnated in a metal and formed into the desired shape. Alternatively, a radioactive powder may be fired to fuse the material so that it may be formed into the desired shape, which may then be encapsulated in metal, such as titanium, stainless steel or silver, or in plastic, as by dipping in molten or uncured plastic. In still another embodiment, the treating elements may be formed from a ceramic material which has been dipped in a radioactive solution. In a still further alternative, the treating elements 22 may be constructed in the form of two piece hollow cylindrical capsules having a larger-diameter half with a central cavity and a smaller-diameter half also having a central cavity, the smaller half slidably received within the larger half and bonded or welded to form the capsule structure.

Turning now to a more detailed description of the catheters of the present invention, as stated previously, catheters of the present invention may be pre-attached to the loading device or, as discussed with regard to FIG. 2, a fitting such as 38 may be provided for attaching an elongated catheter tube to the loading device. Although catheters of the present invention may vary in the number of lumens or the specific construction of such lumens, those catheters have in common, a proximal end attachable to a body member such as body 26, a distal end opposite the body which is adapted to be positioned at a selected site in the body, and an elongated tubular portion therebetween. For those catheters that are not pre-attached to the loading device, the proximal end may be provided with a keyed fitting to allow attachment of only certain catheters to the fitting on the loading device. Such fittings may include those generally known in the art which will not be discussed herein, but also may include specially designed fittings which would be peculiar to this device. A specially keyed fitting would prevent the inadvertent attachment of the fitting or body to other catheters on the market which are not specifically designed to receive the treating elements and/or to prevent the treating elements from being released into the body.

As used herein, the terms "elongated tube," "elongated catheter tube" and similar phrases are intended to include a catheter possessing one or more lumens produced from a single extrusion and catheters of multiple lumens wherein the catheter is made up of several separate tubes bundled together.

Figure 4:
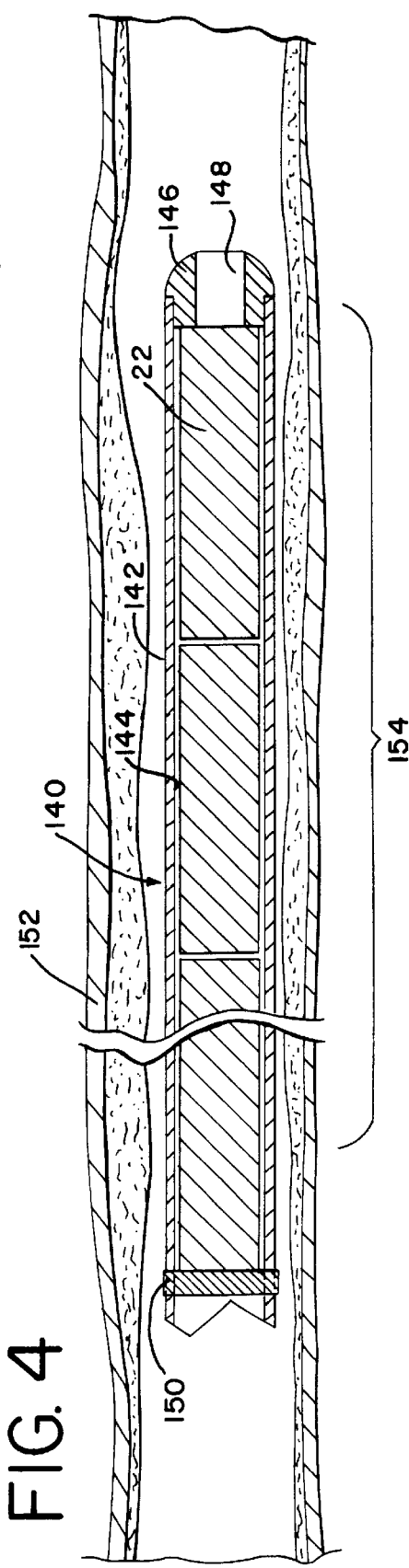
FIG. 4 is a partial cross-sectional view of one embodiment of the elongated catheter tube of the present invention, showing the treating elements disposed in the distal end portion of the tube.

FIG. 4 depicts the distal end portion of one catheter of the present invention, generally at 140, with the treating elements located in the distal end portion. In this embodiment, the catheter comprises a single tubular member 142 having a proximal end portion (not shown), a distal end portion and a lumen 144 extending therebetween. The tubular member is preferably extruded from Nylon 11 material, although other suitable plastic materials may be used. The outer diameter of the tubular member is sized according to the intended application—for example 5 French or smaller for use in treating the stenotic site of a coronary artery. The inner diameter of the lumen is correspondingly sized to receive the treating elements 22.

To prevent treating elements 22 from exiting the distal end of the tubular member, a retention projection may be provided in the lumen to block passage of the treating elements, such as an end barrier 146. Barrier 146 is a separate molded tip adhered or bonded to the distal end portion of tubular member 142. Barrier 146 preferably has a smooth rounded external surface to minimize possible abrasion to a vessel or other tissue and a central opening 148 to allow liquid flow therethrough.

To aid in placement of the catheter at the desired location, a marker band 150 is attached to the outer surface of tubular member 142 at the distal end portion. To provide a continuous smooth outer surface, a slight undercut may be provided in the surface of the catheter tube, in which the marker band resides. Although shown on the exterior surface of the catheter, the marker band may also be provided internally as well. Preferably the barrier 146 and marker band 150 are constructed from barium, a platinum-iridium compound, or like substance, which is visible by fluoroscope during placement of the catheter.

In use, still referring to FIG. 4, the distal end portion of the tubular portion is introduced into the body of a patient into a selected site, such as the coronary artery 152 following balloon angioplasty. In such instances, a guide wire will typically be pre-positioned in the patient, although a guiding catheter could also be used. The distal end of the catheter is then advanced over the guide wire, through lumen 144. The positioning of the device is made more precise due to the ability to fluoroscopically observe the barrier 146 and marker band 150 at the distal end portion of the catheter tube.

After the distal end portion of the catheter is positioned such that the previously stenosed area, generally at 154, of the coronary artery is located between the barrier 146 and marker band 150, the guide wire can be removed, and the proximal end of the catheter can be connected to a treating element loading device and/or pump, as described earlier with reference to the FIGS. 2–2B embodiments.

So connected, the treating elements 22 are in direct communication with lumen 144 of the catheter and a flow path is formed therebetween. Pressurized liquid, such as from a fluid pump, syringe or other piston-cylinder arrangement, plunger, or elevated saline solution container, is then directed against the treating elements, causing them to advance along the catheter lumen until stopped by the end barrier 146.

Referring to the FIG. 2A embodiment of a loading device as an example, to move the treating elements 22 from the body 26 to the selected site in the patient, the carriage 48 is moved from the first position to the second position. This releases the treating elements into the flow path where they are carried rapidly by the motive force of the fluid therein into and through the lumen of the catheter to the distal end portion, which is located at the stenotic site. The rapid transportation of the treating elements reduces the amount of radiation which is transmitted to tissues in the body through which the elongated catheter tube extends. In this embodiment, the liquid transporting the treating elements exits through the central opening 148 in the end barrier 146.

As noted above, upon reaching the distal end portion of the elongated tube, the treating elements are prohibited from being ejected into the patient by the barrier 146. Once more, the barrier and marker band may be used to fluoroscopically visualize the released radioactive elements, and account for their location. The barrier and marker band may be specifically spaced to cover the distance of the lumen occupied by the total length of the radioactive treating elements, and the location of the elements may be confirmed by viewing a solid image between the barrier and marker band on the fluoroscope.

To maintain the treating elements within the distal end portion of the elongated tube, a constant fluid pressure through the lumen and against the treating elements may be required to counteract the effects of external blood pressure and/or gravitational forces exerted upon the treating elements, depending on the angle at which the distal end portion of the elongated tube is placed and on the specific location in the patient.

Preferably, in order to sufficiently irradiate the stenotic site of a coronary artery that has been subjected to PTCA to inhibit intimal hyperplasia, the treating elements should remain at the selected site for a sufficient time to deliver a therapeutically effective amount of radiation, which is preferably between about 100 and 10,000 rads, preferably about 700 to 5,000. The length of time required to deliver this dosage of radiation depends primarily on the strength of the radioactive source used in the treating elements and the number of treating elements employed. The radioactivity needed will depend on the strength of the source used and the emission, and may be in the range of 0.45 to 25,000 mCi depending on the source. After sufficient time, such as 2 to 10 minutes, has been allowed for treatment, the treating elements may be removed by withdrawing the catheter from the patient or by applying suction (such as by a syringe) to the proximal end of the lumen in which the treating element travels.

Figure 5:
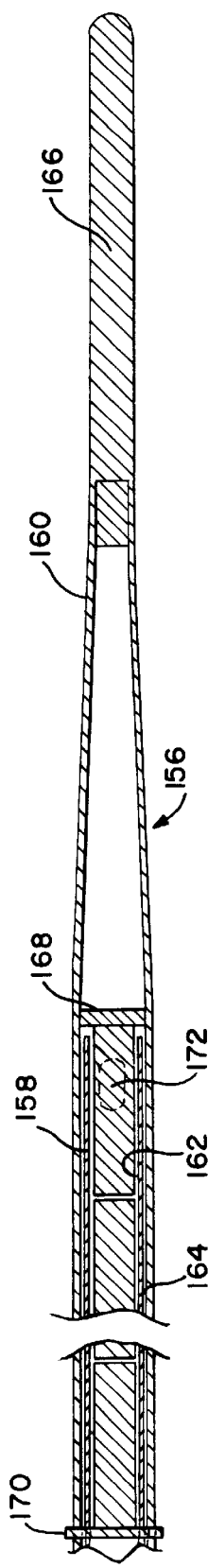
FIG. 5 is a partial cross-sectional view of a second embodiment of the elongated catheter tube of the present invention, showing the treating elements in the distal end portion of the tube.

Another embodiment of an elongated catheter tube 156 of the present invention is shown in FIG. 5. The proximal end of the catheter tube may be pre-attached to a loading device/pump or employ a fitting for keyed attachment to such a device, as described in detail earlier. Accordingly, only the distal end portion of the catheter is depicted in FIG. 5.

As shown in FIG. 5, the elongated tube 156 comprises coaxial inner and outer tubes 158 and 160 respectively. Inner tube 158 defines an inner bore or lumen 162, through which the treating elements 22 are advanced. Inner and outer tubes are spaced apart to define to define a return lumen 164 therebetween for return of the liquid used to advance the treating elements.

The distal end of the outer tube 160 tapers to a narrow, flexible and atraumatic tip 166 bonded to the outer tube. A radiopaque barrier 168 located slightly beyond the end of the inner tube 158 closes the outer tube 160 and blocks further proximal movement of the treating elements 22. Similarly to marker band 150 of the previous embodiment, a marker band 170 may be provided in an undercut area on the surface of outer tube 160 at a location spaced proximally from the barrier 168 to enhance placement of the distal end portion and the treating elements at the desired location.

When used to treat the site of a coronary artery where a balloon angioplasty procedure has been carried out, this catheter 156 is positioned in the previously stenosed site by a guide tube or similar device. Positioning of the distal end portion of the catheter may be viewed fluoroscopically due to the radiopaque barrier 168 and marker band 170.

If not pre-attached to a loading device/pump, the proximal end of the catheter is attached to such a device as described earlier. Without unnecessarily repeating earlier description, the treating elements 22 are advanced along the inner lumen 162 of the catheter under the force of liquid flowing therethrough. With this embodiment, instead of exiting from the distal end of the catheter, the liquid exits from the distal end of the inner lumen (or through a side aperture 172 in the wall of the inner tube), and returns through the return lumen 164 provided between the inner tube and the outer tube. The return liquid may be allowed to exit through the loading device/pump or may be collected therein, as described earlier, for alternative disposal.

Unlike the first embodiment, this embodiment is a completely closed system, in that the fluid is not released into the patient and the treating elements 22 do not contact the blood. While this eliminates the effects of blood pressure in moving the treating elements, a small but constant fluid flow may be required to maintain the treating elements in the distal end portion of the elongated catheter tube due to the gravitational effects in the event the treatment site is at a higher elevation than the proximal end of the catheter. By oscillating the liquid flow between the dispatch and retrieval pistons, the train of treating elements 22 may be shifted slightly back and forth to make the exposure along the desired area more uniform.

The radioactive treating elements remain in the distal end portion of the elongated tube for a sufficient period of time to deliver a therapeutically affective amount of radiation. As was previously discussed, this is preferably about 100–10,000 rads, in the case of inhibiting the development of intimal hyperplasia.

After a sufficient amount of radiation is delivered, the treating elements 22 may be retrieved from the distal end portion of the elongated catheter tube and returned to the loading device by introducing pressurized fluid into the return lumen. This reverses the flow of liquid and creates an oppositely directed motive force on the treating elements forcing them proximally through the inner lumen 162 for return to the loading device. The elongated catheter tube may then be removed from the patient and the procedure concluded. Alternatively, the treating elements may be removed by withdrawing the catheter from the patient.

Figure 6A:
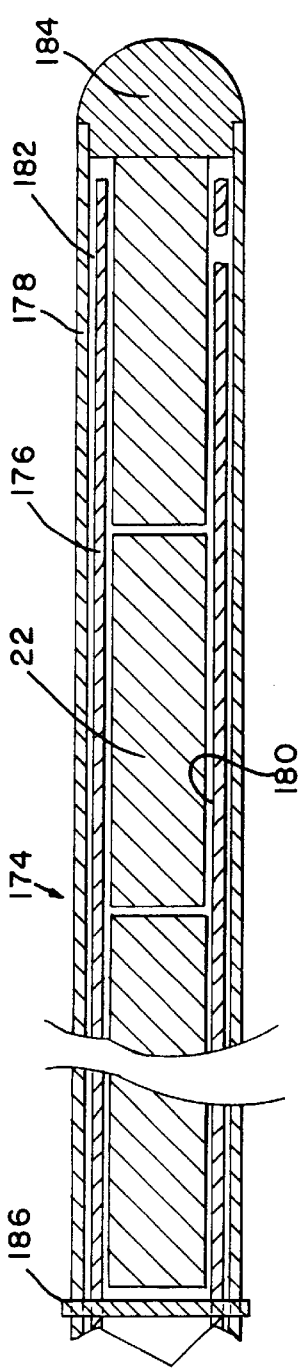
FIG. 6A is a partial cross-sectional view of a third embodiment of the elongated catheter tube of the present invention, showing the treating elements in the distal end portion of the tube.
Figure 6B:
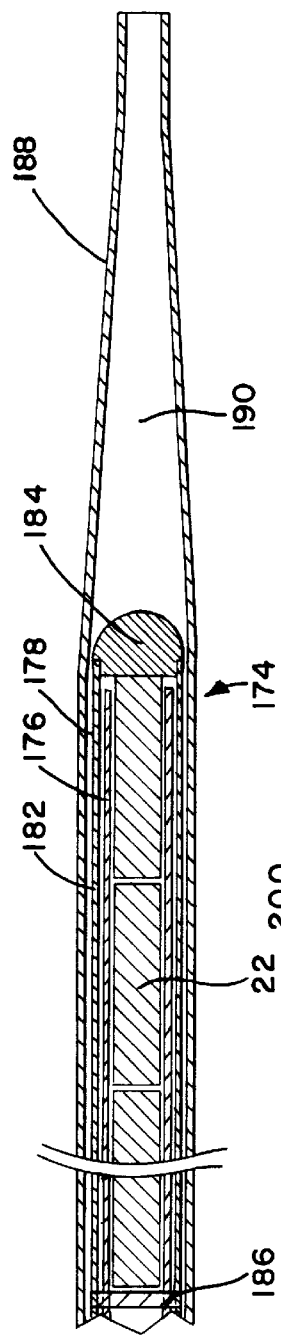
FIG. 6B is a partial cross-sectional view of the FIG. 6A embodiment of the elongated catheter tube of the present invention, disposed within an outer guiding catheter which may be used to position the catheter tube of the present invention within the body of a patient.

In a third alternative embodiment of the present invention shown in FIGS. 6A and 6B, the catheter is constructed and operates similarly to that described for the FIG. 5 embodiment. Elongated catheter tube 174 comprises co-axial inner and outer tubes 176 and 178 respectively. Inner tube 176 defines an inner bore or lumen 180, through which the treating elements 22 are advanced. Inner and outer tubes are spaced apart to define a return lumen 182 therebetween for return of the liquid used to advance the treating elements.

The distal end of the outer tube 178 is not tapered, but is closed by radiopaque solid tip 184, which also serves as a barrier to the treating elements as they move along the inner lumen 180. Also similarly, a marker band 186 is provided on the surface of outer tube 178 at a location spaced proximally from the tip 174 to enhance placement of the distal end portion and the treating elements at the desired location.

The initial placement of the distal end portion of elongated catheter tube 174 is facilitated by the use of a third or guide tube 188, as is shown in FIG. 6B. As shown therein, the separate third tube 188 has a proximal end portion (not shown), a tapered distal end portion and a lumen 190 extending therebetween.

In use, the guide tube has sufficient strength or rigidity for placement or is placed into the body of a patient over a pre-positioned guide wire, so that the distal end portion of the third tubular member is located at a specific selected site within the body at which treatment is desired. Once the guide tube is positioned at the selected site, and the guide wire at least partially pulled back, the elongated catheter tube 174 shown in FIG. 6A may be inserted into lumen 190 of the guide tube.

As in the FIG. 5 embodiment, the embodiment shown in FIGS. 6A and 6B allows treating elements 22 to be hydraulically moved between the proximal and distal end portions of the elongated tube, with the direction of the hydraulic flow being determined by the pressure gradient existing between the delivery and retrieval lumens. Thus, after maintaining the treating elements at the distal end portion of the elongated catheter tube for a desired period of time, the treating elements may be retrieved by reversing the flow of fluid through the elongated tube. Following this the catheter and third or guide tube may be removed from the patient and the procedure concluded.

Figure 7A:
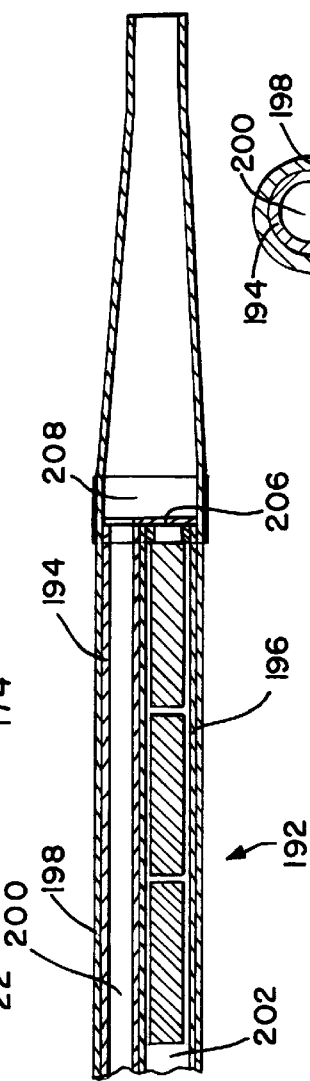
FIG. 7A is a partial cross-sectional view of a fourth embodiment of the elongated catheter tube of the present invention, showing the treating elements disposed in the distal end portion of the tube.
Figure 7B:
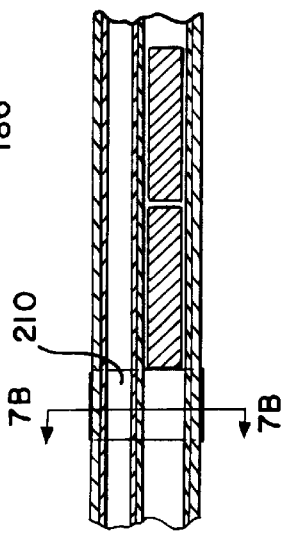
FIG. 7B is a partial cross-sectional view of the elongated catheter tube of FIG. 7A taken along line 7–7B.

Another embodiment of the catheter of the present invention, particularly intended for placement at a desired location by advancement over a guide wire, is shown in FIGS. 7A and 7B. The elongated catheter tube 192 comprises a pair of inner tubes 194 and 196 that extend in a parallel side-by-side arrangement within an outer tube 198. Inner tube 194, which is of smaller diameter than tube 196, defines an inner lumen 200 for receiving a guide wire used for placement of the catheter at the desired location within the patient. Inner tube 196, which is of larger diameter, provides inner lumen 202 along which the treating elements 22 travel. Return lumen 204 is provided by the space between the inner surface of the outer tube 198 and the outer surfaces of the inner tubes 194 and 196 for return flow of liquid used to transport the treating elements.

As seen in FIG. 7A, the outer tube 198 has an open tapered distal end. An interluminal wall 206 is provided within the outer tube at the beginning of the taper and at the distal end of the inner tubes 194 and 196. The wall 206 includes an aperture in sealed communication with lumen 200 of inner tube 194, through which a guide wire may pass. The wall 206 is preferably slightly spaced from the distal end of the other inner tube 196, through which the treating elements pass, to allow liquid to exit from the end of tube 196 for return through the return lumen 206. The wall also provides a barrier to prevent the treating elements from exiting the end of tube 196.

As in the earlier embodiments, the elongated catheter tube 192 has first and second radiopaque marker bands, 208 and 210 on the outer tube to aid in placing the distal end portion at the desired location in the patient. As noted earlier, although generally depicted on the outer tube in many of the embodiments, the markers may be provided inside the catheter at any convenient location, such as on an inner tube or surface, without departing from the present invention.

In use for treating a stenotic site in a coronary artery with radiation, the proximal end of the elongated catheter 192 tube may be pre-connected to a loading device/pump or separately connected to such a device by a keyed fitting or similar arrangement, as discussed earlier. The distal end portion of the elongated catheter tube is then positioned at the selected site within the body of the patient by advancing the catheter over a pre-positioned guide wire. In this embodiment, the guide wire may be allowed to remain in position. This has the significant advantage that it is unnecessary to insert the guide wire a second time if a further catheter or device needs to be inserted after the treatment is completed.

The radiopaque marker bands 208 and 210 are visible on a fluoroscope and aid in the placement of the device. When the distal end portion of the elongated tube is positioned such that the selected site is located between marker bands 208 and 210, liquid may be pumped through the lumen 202 to move the treating elements to the distal end portion of the elongated catheter tube, where they are accounted for by the positioning of the marker bands. After sufficient irradiation has occurred, the flow through the device is reversed by reversing the flow of pressurized fluid through the return lumen causing return of the treating elements to the loading device. The elongated catheter tube may then be removed from the patient and the procedure completed.

A further alternative embodiment of the catheter of the present invention, preferably intended for placement over a guide wire, is shown in FIGS. 8A and 8B. The elongated catheter tube 212 comprises a pair of inner tubes 214 and 216 that extend in a parallel side-by-side arrangement within an outer tube 218. As in the FIG. 7 embodiment, inner tube 214, which is of smaller 26 diameter than tube 216, defines an inner lumen 220 for receiving a guide wire used for placement of the catheter at the desired location within the patient. Inner tube 216, which is of larger diameter, provides inner lumen 222 along which the treating elements 22 travel. A return lumen 224 is provided by the space between the inner surface of the outer tube 218 and the outer surfaces of the inner tubes 214 and 216 for return flow of liquid used to transport the treating elements, in the very same manner as depicted in FIG. 7B. In the FIG. 8 embodiment, however, inner tube 214 (for the guide wire) extends fully along the length of the outer tube 218, and is bonded to the outer tube at the distal-most location, where the outer tube is tapered.

In FIG. 8A, an internal barrier 226 is provided at the end of the inner tube 216, through which the treating elements are carried, to block the passage of treating elements from the distal end of the tube 216. A center opening in the barrier 226 allows liquid to pass from the lumen 222 of the inner tube 216 to the return lumen. Alternatively, the barrier may be solid as depicted with barrier 228 in FIG. 8B (which is otherwise the same as FIG. 8A), and an aperture 230 may be provided in the wall of inner tube 216 to permit liquid to flow between the treating element lumen 222 and the return lumen. Although not depicted in FIG. 8A or 8B, it should be understood that the elongated catheter tube may also include a series of marker bands appropriately placed along the length of the tube to aid in accurate placement in the patient.

Another embodiment of the catheter of the present invention is shown in FIG. 9. As shown there, catheter 232 has three co-axial tubes, inner tube 234, outer tube 236 and intermediate tube 238, which all extend the full length of the catheter. Inner tube 234 has a lumen 240 for receiving a guide wire for placement of the catheter at the desired location in the patient. Inner tube 234 is spaced from intermediate tube 238 to define an annular treating element passageway 242 therebetween. In this embodiment, the treating elements are preferably ring shaped, as at 244, or donut shaped, as at 246, to allow them to slide over the inner tube 234 and along the passageway 242. To provide a return flow channel, the inner diameter of the outer tube 236 is slightly larger than the intermediate tube 238 to provide a return flow path 248 therebetween.

The end of the catheter is closed by a molded tip plug 250, preferably of radiopaque material, bonded to the ends of the inner and outer tubes 234 and 236. Center passageway 252 through the tip plug allows for the passage of a guide wire or the like for placement of the catheter at the desired location. The distal end of the intermediate tube 238 stops short of the tip plug, thereby allowing the treating element passageway 242 to communicate directly with the return flow path 248. Radiopaque marker bands, although not shown, may also be incorporated on the distal end portion of the elongated catheter tube to aid in placing the elongated tube within the body at the selected site.

After the distal end portion of the elongated tube is positioned at the desired location in the patient, a liquid, such as saline, is forced through the treating element passageway 242 and directed against the ring-shaped treating elements, moving the treating elements along the passageway over the inner tube 234 until they abut the distal tip plug 250. The radioactive elements are retained at the distal end portion of the elongated catheter tube for a sufficient time to deliver the therapeutically effective amount of radiation to the selected site. To retrieve the treating elements, the fluid flow is reversed through the flow path by forcing liquid in a distal direction through the return lumen. Following this the elongated tube can be removed over the guide wire and the procedure completed.

In a still further embodiment of the present invention, shown in FIG. 10, a catheter 254 is provided which includes both an inflatable balloon membrane 256 for carrying out a balloon angioplasty procedure and treating elements 22 fixed in the distal end of the catheter for simultaneous treatment. The catheter of FIG. 10 includes an elongated tubular portion 258, typically of extruded construction, with a guide wire lumen 260 and an inflation lumen 262. A balloon membrane is located at the distal end of the catheter tube and sealed to the exterior surface to form an inflatable balloon. Port 264 communicates between the inflation lumen and the inside of the balloon for inflating the balloon by pressurized liquid. Only the distal end portion of the catheter is shown—the proximal end of the catheter being typical of angioplasty catheter construction as is well known to those skilled in the field.

To perform radiation treatment simultaneously with a balloon angioplasty procedure, radioactive treating elements 22 are located within the balloon, between coaxial walls 266 and 268 of the distal end portion of the catheter. The treating elements are ring-shaped or donut-shaped, as described earlier, and positioned over the inner wall 266. Stop rings 270, preferably of radiopaque material, are positioned at each end of the string of treatment elements to maintain the treatment elements at a fixed location within the balloon and aid in locating the catheter at the desired location.

The strength and other characteristics of the radioactive treating elements are essentially as described earlier and will not be repeated. With this construction, the balloon angioplasty procedure and the radiation treatment of the stenotic site may be carried out simultaneously instead of sequentially, thereby further reducing the time, cost and risk associated with such procedures.

In use, catheter 254 is positioned into the stenosed area of the artery over a pre-positioned guide wire. Using the radioactive treating elements alone or in conjunction with the radiopaque end rings, the distal end portion of the catheter is positioned such that the balloon portion is located at the stenosed site. Pressurized fluid introduced into the proximal end of the inflation lumen, as with a syringe, enters through port 264, inflating the balloon. The expanding balloon membrane 256 compresses the sclerotic plaque and increases the diameter of the blood vessel. The balloon may be deflated and the distal tip retained in this position for the desired period of time to deliver an effective amount of radiation to the previously stenosed area. The device may then be removed from the patient and the procedure completed.

FIG. 11 shows a variation of the radiation delivery system of FIG. 10. In the FIG. 11 embodiment, the basic operation and construction of the catheter are the same as described with respect to that shown in FIG. 10, except that in FIG. 11, the radioactive treating elements are located on inner tube 272 and directly below balloon membrane 274. Balloon membrane may be inflated by the introduction of pressurized fluid through inflation lumen 276 defined between inner tube 272 and co-axial outer tube 278.

FIG. 12 shows the distal end portion of another balloon catheter 280 embodying the present invention. The catheter 280 employs three coaxial tubes, inner tube 282, outer tube 284 and intermediate tube 286. Inner tube 282 defines an inner lumen 288 through which a guide wire may extend for placement of the catheter at the desired location. The space between the inner tube and the intermediate tube 286 defines an annular lumen 290, through which ring-shaped or donut-shaped treating elements may pass. The space between the intermediate tube and the outer tube 284 forms a return lumen 292 for return of liquid used to transport the treating elements.

The catheter 280 also includes a balloon membrane 294 bonded at one end to the exterior surface of the outer tube 284 and bonded to the exterior surface of the inner tube 282 (which extends beyond the distal ends of the intermediate and outer tubes) at the other end. The distal end of the outer tube is closed by a barrier 296, which may be radiopaque, to block the exit of the treating elements from the distal end of lumen 290. In this embodiment, the same liquid used to transport the treating elements is also used to inflate the balloon membrane, although that is not required if a separate inflation lumen were provided. To inflate the balloon membrane, a side opening 298 or port is provided in the wall of the outer tube 284 and also in the intermediate tube 286 if desired. With this construction, pressurized blood-compatible liquid, such as sterile saline, may be used to advance the treating elements while simultaneously advancing the treating elements to the distal end portion of the catheter. The treating elements may be retrieved by reversing the flow of the liquid through the return and treating element lumen 292 and 290, respectively. Further release of pressure exerted upon the liquid will allow the balloon to deflate and the catheter to be removed.

Figure 13:
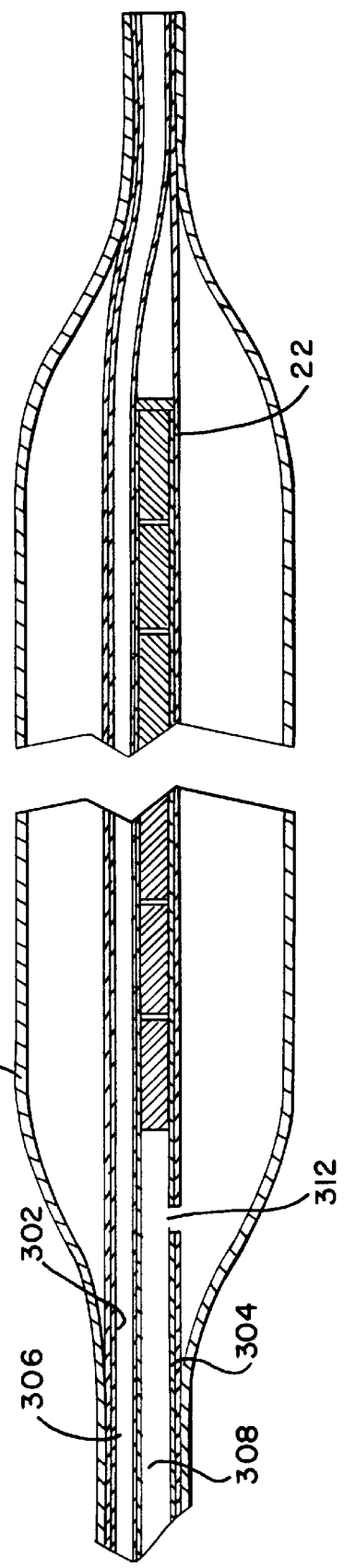
FIG. 13 is a partial cross-sectional view of a further alternative embodiment of the present invention having an inflatable balloon, with the treating elements movable along the catheter.

FIG. 13 illustrates a still further embodiment of a balloon catheter 300 which has a pair of adjacent parallel inner tubes, 302 and 304, forming guide wire lumen 306 and a treating element lumen 308. In a manner similar to FIGS. 7 and 8, the inner tubes are contained within an outer tube, and the interior space therebetween forms a return lumen. A balloon membrane 310 is bonded to the outer surface of the outer tube, forming an inflatable balloon. The balloon membrane may be inflated, through side port 312 in the wall of inner tube 304, by the same blood-compatible liquid that is used to propel the treating elements along the lumen 308. As in FIG. 12, this catheter permits expansion of the balloon membrane to carry out an angioplasty procedure within a blood vessel at the same time the treating elements are being moved to the distal end portion of the catheter (where the balloon is located) to effect radiation treatment of the tissue being subjected to the balloon angioplasty procedure.

Figure 14:
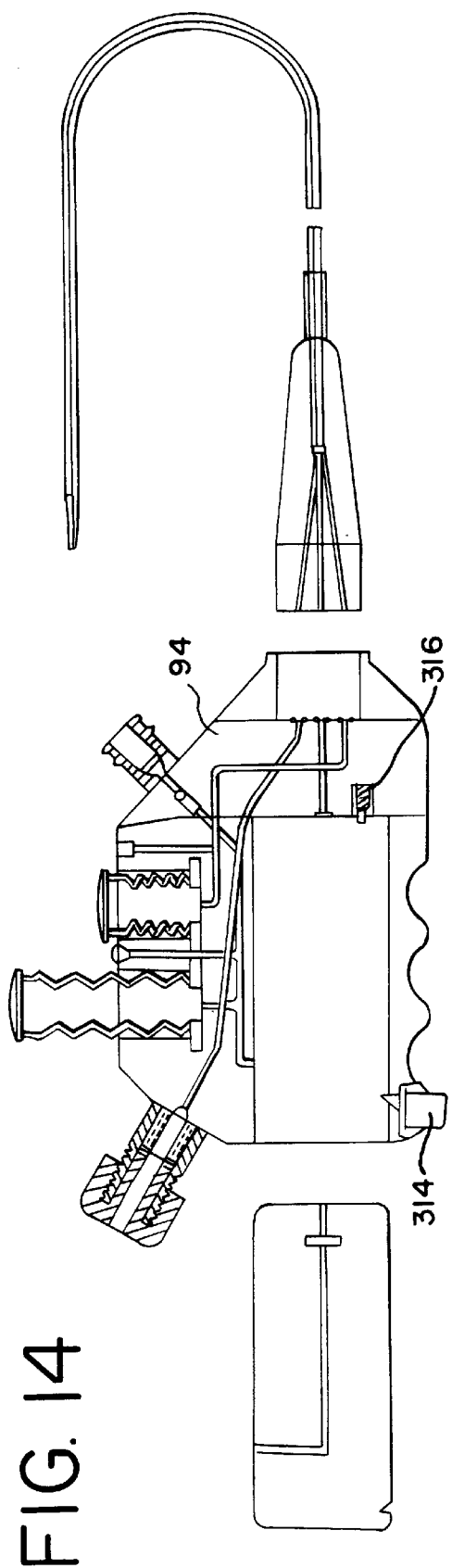
FIG. 14 is a partial cross-sectional view of another embodiment of the treatment delivery system of the present invention.

FIG. 14 shows a device that is essentially identical to that shown in FIG. 2C and described in detail earlier, except that the body member 94 includes a latch 314, such as spring loaded pin, to retain insert 110 within chamber of cavity 108. A release mechanism 316 may also be provided to release the insert.

FIGS. 15A–15C show another embodiment of treatment delivery system that is similar in many respects to the embodiment shown in FIG. 2C. In this embodiment, however, the gate 114 is in the form of a disc 318 pivotally mounted at the distal end of the insert 110. The disc includes a pair of spaced-apart apertures 320 and 322, of different sizes, therethrough, which may be moved into alignment with the center bore 112 of the insert. One of the apertures 320 is smaller in diameter than the treating elements 22, and when aligned with the bore 112 blocks the passage of treating elements from the bore while allowing liquid to pass therethrough for priming and the like. Alternatively, the disc may be pivoted to a position where the larger aperture 322 is aligned with the center bore 112, which allows the treating elements to be ejected from the insert by liquid flow pressure and advanced into and through the catheter. For shipment and storage, the disc may be positioned to fully cover the bore 112 of the insert.

In this embodiment, the body 94 includes a pair of opposed side access openings 324 for accessing the disc 318 to pivot it between the desired positions, and a pair of opposed viewing access openings 326 for visually verifying the location of the treating elements. In this embodiment, the catheter 92 has a proximal fitting 328 for attachment to the distal end of the body 94. This fitting may be keyed to assure that it is attached in the proper relationship to the body and the correct lumen of the catheter are aligned with the proper passageways of the body.

Figure 16:
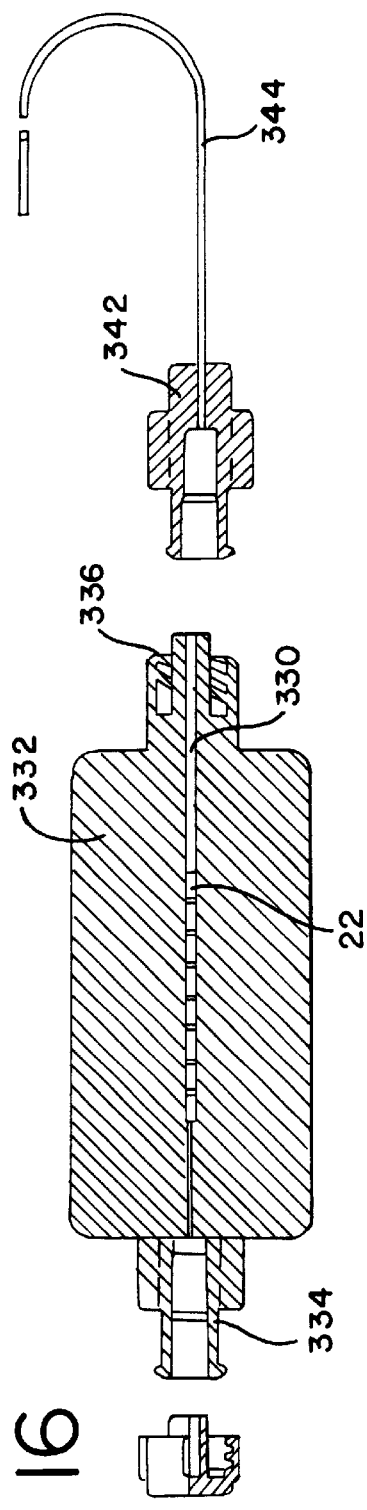
FIG. 16 is a partial cross-sectional view of various parts of a further embodiment of the treatment delivery system of the present invention.

FIG. 16 shows a simplified version of the treating system of the present invention. As shown there, the treating elements 22 are contained in a central passageway 330 of a solid body 332. Female luer lock connector 334 is provided at the inlet end of the passageway and male luer lock connector 336 is provided at the outlet end of the passageway, although a keyed fitting as described above also may be used.

During travel and storage a temporary female luer lock connector 338 is attached to the outlet connector 336. The connector 338 includes a pin 340 that extends from the connector into the passageway to hold the treating elements in place and provide a barrier against the escape of radiation. The inlet end of the passageway is smaller than the treating elements, thereby keeping the treating elements located in generally the center of the body 332.

To use this embodiment, the temporary connector 338 is removed and a female luer lock connector (or keyed connector, as discussed above) connector 342 at the proximal end of single lumen catheter 344 is attached to the outlet connector 336. A source, such as a syringe or suspended container, of blood-compatible liquid, such as saline, is attached to the inlet connector 334, and liquid is allowed to flow through the center passageway, ejecting the treating elements 22 and forcing them along the length of the catheter from the proximal to the distal end portion, which is presumable located at the site in the vascular system where treatment is desired. After the treatment is complete, the treating elements are removed by withdrawing the catheter from the patient's body or by applying a suction to the proximal end to return the treating elements by the force of reversed liquid flow.

Figure 17:
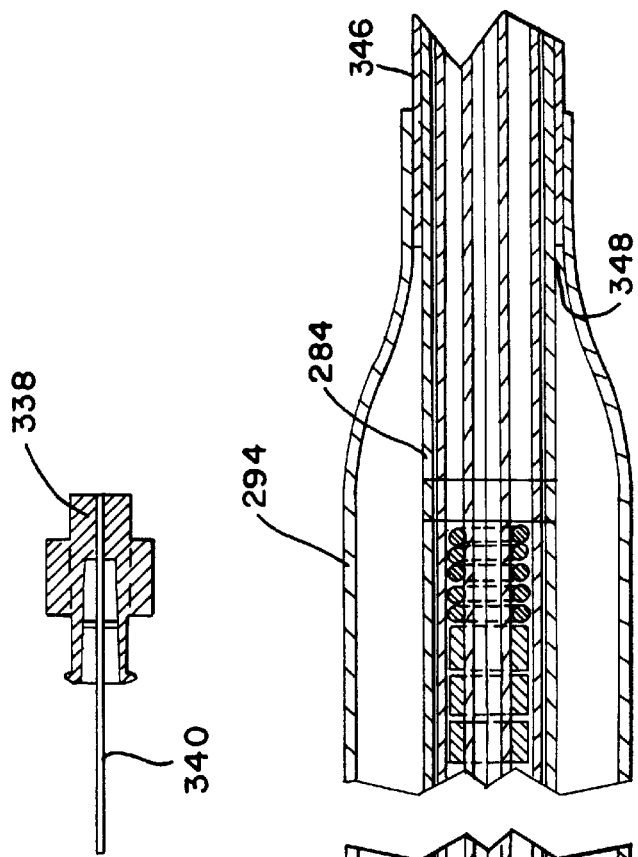
FIG. 17 is a partial cross-sectional view of another alternative embodiment of the present invention having an inflatable balloon, with the treating elements movable along the catheter.

FIG. 17 is identical to FIG. 12, except that a fourth co-axial outer tube 346 is provided over tube 284, and the end of the balloon membrane 294 is bonded to the outer tube 346 instead of the tube 284. The distal end of the outermost tube 346 terminates just inside the balloon membrane, and the space between the outermost tube 346 and the tube 284 provides an inflation lumen 348 through which pressurized fluid may flow directly into the area beneath the membrane to inflate the balloon. This construction allows a separate source of pressurized fluid to be used to inflate the balloon membrane, and inflation of the balloon membrane is not dependent on the pressure of the liquid used to move the treating elements to the distal end portion of the catheter.

Similarly, FIG. 18 is identical to FIG. 13, except that an additional tube 350 is provided over the other tubes described in connection with FIG. 13, and one end of the balloon membrane 310 is bonded to surface of the tube 350. As with FIG. 17, the space between the additional tube 350 and the tubes described earlier provides an inflation lumen 352, the distal end of which lumen opens directly in the area beneath the balloon membrane. This construction also allows a source of fluid, independent of the liquid used to move the treating elements, to be used to inflate the membrane in carrying out an angioplasty procedure.

FIG. 19 shows a still further embodiment of the distal end portion of a catheter 354 having an elongated inner tube 356 (which extends from a proximal end portion, not shown) defining an inner lumen 358. The inner tube 356 extends co-axially within an outer tube 360, the distal end of which stops short of the distal end of the inner tube. Balloon membrane 362 is attached at one end to the surface of outer tube 360 and is attached at the other end to the surface of the inner tube 356. The space between the inner and outer tubes forms an inflation lumen 364, through which liquid may be introduced to inflate the balloon.

A separate elongated catheter tube 364 is insertable into inner lumen 358 such that the distal end portion of the separate tube lies within the area of the balloon. The separate tube also has a lumen 366 extending from the proximal end (not shown) through which treating elements 22 are movable under the force of flowing liquid from the proximal to the distal end portion of the catheter (the liquid in this embodiment exits through the distal end of the lumen 358).

Although the present invention has been described in terms of certain specific embodiments, it is understood that various changes and modifications may be made without departing from the present invention, and reference should be made to the appended claims to determine the proper scope of this invention.

What is claimed is:

1. An apparatus for treating a selected area of the vascular system of a patient comprising:

at least one elongated flexible tube including a proximal end and a distal end for positioning at the selected area of the vascular system and defining first, second, third, and fourth lumens, said first, second, and third lumens extending in generally parallel relationship between said proximal and distal ends of said tube, said second and third lumens being in fluid-tight communication at said distal end of said tube, said fourth lumen being open at said distal end of said tube for receiving a guidewire, and a flexible balloon membrane carried at said distal end of said tube, said balloon membrane being in fluid communication with said first lumen for inflation when pressurized fluid is introduced through said first lumen.

2. The apparatus of claim 1 wherein said second lumen has a diameter sufficiently large between said proximal and distal ends of said tube to permit slidable passage of at least one treating element between said proximal and distal ends, whereby said at least one treating element may be moved between said proximal and distal ends of said tube through said second lumen under the force of pressurized fluid flowing through said second and third lumens.

3. The apparatus of claim 1 wherein said tube comprises four conjoined coaxial plastic tubes each having a proximal and a distal end, with the spaces between said coaxial tubes defining said first, second, and third lumens, and the coaxial tube that is innermost having a lumen comprising said fourth lumen.

4. The apparatus of claim 3 wherein the distal end of the outermost coaxial tube terminates inside said balloon membrane.

5. The apparatus of claim 1 further comprising a second separate elongated flexible tube including a proximal end and a distal end, said second tube being substantially coextensive in length with said at least one tube, wherein said at least one tube defines said first lumen and further defines a fifth lumen sized to receive said second tube, and said second tube defines said second, third, and fourth lumens.

6. The apparatus of claim 5 wherein said second separate tube is of sufficiently small diameter for advancing through the vascular system and into a coronary artery and of sufficient flexibility to follow a guidewire through the vascular system and into the coronary artery, with said second and third lumens being parallel and extending substantially co-extensively through said second separate tube between said proximal and distal ends.

7. The apparatus of claim 6 further comprising at least one radiopaque marker on said distal end of said second separate tube.

8. A method for treating a selected area of a coronary artery in a human patient that is to be subjected to an opening procedure, said method comprising:
   a) providing at least one elongated tube having a proximal end and a distal end and defining first, second, third, and fourth lumens, said first, second, and third lumens extending between said proximal and distal ends of said tube, said second and third lumens being in fluid-tight communication at said distal end of said tube, said fourth lumen being open at said distal end of said tube for receiving a guidewire, and
      a flexible balloon membrane carried at said distal end of said tube, said balloon membrane being in fluid communication with said first lumen for inflation when pressurized fluid is introduced through said first lumen,
   b) providing at least one treating element slidably receivable in said second lumen and movable from said proximal end of said tube to said distal end when fluid is directed through said second lumen and movable from said distal end of said tube to said proximal end when fluid is directed into said third lumen,
   c) advancing said distal end of said fourth lumen through the vascular system of the patient to the selected area by advancing said fourth lumen over a guidewire that extends to the selected area,
   d) inflating said balloon by directing fluid into said first lumen,
   e) advancing said treating element to the selected area through said second lumen by directing a fluid through said second and third lumens in a forward direction, and
   f) allowing said treating element to remain in the selected area for a therapeutically effective amount of time.

9. The method of claim 8 further comprising:
   a) retrieving said treating element from the selected area and returning it to said proximal end of said tube by directing fluid flow through said third and second lumens in a reverse direction, and
   b) withdrawing said tube from the artery of the patient.

10. The method of claim 8 further comprising providing said at least one elongated tube wherein said tube comprises four conjoined coaxial tubes each having a proximal and a distal end, with the spaces between said coaxial tubes defining said first, second, and third lumens, and the coaxial tube that is innermost having a lumen comprising said fourth lumen.

11. The method of claim 8 further comprising:
   a) providing a second tube having a proximal end and a distal end substantially coextensive with said at least one tube, wherein said at least one tube defines said first lumen and further defines a fifth lumen sized to receive said second tube, and said second tube defines said second, third, and fourth lumens,
   b) advancing said second tube to the selected area within said fifth lumen of at least one tube after said balloon has been inflated.

12. An apparatus for treating a selected area of the vascular system of a patient comprising:
   an elongated tube having a proximal end portion, a distal end portion opposite said proximal end portion and first and second lumens extending therebetween;
   a flexible balloon membrane carried at said distal end portion of said elongated tube, said balloon membrane being in communication with said first lumen for inflation when pressurized fluid is introduced through said first lumen; and
   a radioactive treating element carried within said second lumen and moveable between said proximal and distal end portions by means of pressurized fluid introduced through said second lumen.

13. An apparatus for treating a selected area of the vascular system of a patient comprising:
   an elongated flexible tube including a proximal end and a distal end for positioning at the selected area of the vascular system and defining first, second and third lumens,
   said first, second and third lumens extending in generally parallel relationship between said proximal and distal ends of said tube,
      said first lumen being open at said distal end of said tube for receiving a guidewire,
      said second and third lumens being in fluid-tight communication at said distal end of said tube, and
   a flexible balloon membrane carried at said distal end of said tube, said balloon membrane being in fluid communication with one of said second and third lumens for inflation when pressurized fluid is introduced through said second and third lumens;
   said second lumen having a diameter sufficiently large between said proximal and distal ends of said tube to permit slidable passage of at least one treating element between said proximal and distal ends, whereby said at least one treating element may be moved between said proximal and distal ends of said tube through said second lumen under the force of pressurized fluid flowing through said second and third lumens.

14. The apparatus of claim 13 wherein said tube comprises three conjoined coaxial plastic tubes each having a proximal and a distal end, with the spaces between said coaxial tubes defining said second and third lumens, and the coaxial tube that is innermost having a lumen comprising said first lumen.

15. The apparatus of claim 14 wherein the distal end of the outermost coaxial tube terminates inside said balloon membrane.

16. The apparatus of claim 13 wherein said tube comprises two adjacent inner tubes contained within an outer tube, said inner tubes defining said first and second lumens and said outer tube defining said third lumen.

17. The apparatus of claims 14 further comprising at least one radiopaque marker on said distal end of said outermost tube.

18. The apparatus of claims 16 further comprising at least one radiopaque marker on said distal end of said outermost tube.

19. A method for treating a selected area of a coronary artery in a human patient that is to be subjected to an opening procedure, said method comprising:
   a) providing an elongated flexible tube having a proximal end and a distal end and defining first, second and third lumens, said first, second and third lumens extending between said proximal and distal ends of said tube, said first lumen being open at said distal end of said tube for receiving a guidewire, said second and third lumens being in fluid-tight communication at said distal end of said tube, and a flexible balloon membrane carried at said distal end of said tube, said balloon membrane being in fluid communication with one of said second and third lumens for inflation when pressurized fluid is introduced through said second and third lumens,
   b) providing at least one treating element slidably receivable in said second lumen and movable from said proximal end of said tube to said distal end of said tube when pressurized fluid is directed through said second lumen and movable from said distal end of said tube to said proximal end of said tube when pressurized fluid is directed into said third lumen,
   c) advancing said distal end of said tube through the vascular system of the patient to the selected area by advancing said first lumen over a guidewire that extends to the selected area,
   d) inflating said balloon by directing pressurized fluid into said second and third lumens,
   e) advancing said treating element to the selected area through said second lumen by directing pressurized fluid through said second and third lumens in a forward direction, and
   f) allowing said treating element to remain in the selected area for a therapeutically effective amount of time.

20. The method of claim 19 further comprising:
   a) retrieving said treating element from the selected area and returning it to said proximal end of said tube by directing pressurized fluid flow through said third and second lumens in a reverse direction, and
   b) withdrawing said tube from the artery of the patient.

21. The method of claim 19 further comprising providing said elongated tube wherein said tube comprises three conjoined coaxial tubes each having a proximal and a distal end, with the spaces between said coaxial tubes defining said second and third lumens, and the innermost coaxial tube having a lumen comprising said first lumen.

22. The method of claim 19 further comprising providing said elongated tube wherein said tube comprises two adjacent inner tubes contained within an outer tube, said inner tubes defining said first and second lumens and said outer tube defining said third lumen.

23. An apparatus for treating a selected area of the vascular system of a patient by means of at least one treating element transported to the selected area by pressurized fluid, the apparatus comprising:
   inner, outer, and intermediate spaced-apart, elongated, flexible coaxial tubes, each tube having a proximal end and a distal end for positioning at the selected area of the vascular system;
   the coaxial tubes defining a first lumen interior of the inner tube, a second lumen interior of the intermediate tube and exterior of the inner tube, and a third lumen interior of the outer tube and exterior of the intermediate tube;
   the first lumen being open at its distal end for receiving a guidewire and one of said second and third lumens being adapted to transport a treating element between the proximal and distal ends of the tube by pressurized fluid; and
   a flexible balloon membrane carried at the distal ends of the coaxial tubes, the balloon membrane being in fluid communication with the third lumen for inflation by the pressurized fluid used for transporting the treating element.

24. The apparatus of claim 23 wherein the balloon membrane has proximal and distal ends, the proximal end of the balloon membrane being secured to the outer tube and the distal end of the balloon membrane being secured to the inner tube, the distal end of the inner tube extending beyond the distal ends of the outer tube and the intermediate tube.

25. The apparatus of claim 23 wherein the distal ends of the outer tube and intermediate tube are closed by a barrier adapted to block the exit of the treating element.

26. The apparatus of claim 25 wherein the barrier is a radiopaque material.

27. An apparatus for treating a selected area of the vascular system of a patient by means of at least one treating element transported to the selected area by pressurized fluid, the apparatus comprising:
   a first elongated flexible tube having a proximal end and a distal end and defining a first lumen, the distal end of the first lumen being open for receiving a guidewire;
   a second elongated flexible tube having a proximal end and a distal end and defining a second lumen, the second tube being in parallel relationship with the first tube and adapted to transport a treating element between the proximal end and distal end by pressurized fluid;
   a third, outer elongated, flexible tube having a proximal end and a distal end and containing the first and second tubes, a third lumen being defined interior of the outer tube and exterior of the first and second tubes, the second lumen and the third lumen being in fluid communication to permit transport of the treating element between the proximal and distal ends of the second tube; and
   a flexible balloon membrane carried at the distal ends of the tubes, the balloon membrane being in fluid communication with the third lumen for inflation by the pressurized fluid used for transporting the treating element.

* * * * *